(12) United States Patent
Cohen

(10) Patent No.: US 10,905,716 B2
(45) Date of Patent: Feb. 2, 2021

(54) MODIFIED BLOOD CLOTS

(71) Applicant: NAYACURE THERAPEUTICS LTD., Bet Hananya (IL)

(72) Inventor: Shahar Cohen, Kiryat Bialik (IL)

(73) Assignee: NAYACURE THERAPEUTICS LTD., Bet Hananya (IL)

( * ) Notice: Subject to any disclaimer, the term of this patent is extended or adjusted under 35 U.S.C. 154(b) by 0 days.

(21) Appl. No.: 15/551,483

(22) PCT Filed: Feb. 16, 2016

(86) PCT No.: PCT/IL2016/050185
§ 371 (c)(1),
(2) Date: Aug. 16, 2017

(87) PCT Pub. No.: WO2016/132357
PCT Pub. Date: Aug. 25, 2016

(65) Prior Publication Data
US 2018/0021375 A1    Jan. 25, 2018

Related U.S. Application Data

(60) Provisional application No. 62/134,641, filed on Mar. 18, 2015, provisional application No. 62/116,851, filed on Feb. 16, 2015.

(51) Int. Cl.
| | | |
|---|---|---|
| *A61K 35/14* | (2015.01) | |
| *A61L 27/36* | (2006.01) | |
| *A61K 35/51* | (2015.01) | |
| *A61L 26/00* | (2006.01) | |

(52) U.S. Cl.
CPC .............. *A61K 35/14* (2013.01); *A61K 35/51* (2013.01); *A61L 26/0057* (2013.01); *A61L 27/3616* (2013.01); *A61L 2400/04* (2013.01); *A61L 2400/06* (2013.01)

(58) Field of Classification Search
CPC .. A61K 35/14; A61L 27/3616; A61L 26/0057
See application file for complete search history.

(56) References Cited

U.S. PATENT DOCUMENTS

| 7,125,569 B2 | 10/2006 | Nur et al. |
|---|---|---|
| 2001/0034851 A1 | 10/2001 | Randahl et al. |
| 2014/0274893 A1 * | 9/2014 | Woodell-May ........ A61K 38/00 514/7.6 |

FOREIGN PATENT DOCUMENTS

| EP | 2781224 | 9/2014 | |
|---|---|---|---|
| WO | 1993/005822 A1 | 4/1993 | |
| WO | 2007/050902 | 5/2007 | |
| WO | WO-2007050902 A1 * | 5/2007 | ......... A61L 27/3604 |
| WO | 2008/081463 | 7/2008 | |
| WO | 2009/087560 A1 | 7/2009 | |
| WO | 2009/098698 A2 | 8/2009 | |
| WO | 2010/100570 A2 | 9/2010 | |
| WO | 2013/003356 A1 | 1/2013 | |
| WO | 2015/128858 A1 | 9/2015 | |

OTHER PUBLICATIONS

Duhamel et al. A simple procedure for the purification of bovine fibrin from clotted blood by the use of detergents. Prep Biochem. 1980;10(1):43-57. (Year: 1980) Abstract only.*
Duhamel et al. A Simple Procedure for the Purification of Bovine Fibrin From Clotted Blood by the Use of Detergents. Preparative Biochemistry , 10(1), 43-57 (Year: 1980).*
Gale AJ. Current Understanding of Hemostasis. Toxicologic pathology. 2011;39(1):273-280.
Mosesson MW. Fibrinogen and fibrin structure and functions. J Thromb Haemost. Aug. 2005; 3(8):1894-904.
Dickneite G, Metzner H, Pfeifer T, Kroez M, Witzke G. A comparison of fibrin sealants in relation to their in vitro and in vivo properties. Thromb Res. 2003; 112(1-2):73-82.
Blair P, Flaumenhaft R. Platelet α—granules: Basic biology and clinical correlates. Blood reviews. 2009; 23(4):177-189.
Dohan Ehrenfest DM, Rasmusson L, Albrektsson T. Classification of platelet concentrates: from pure platelet-rich plasma (P-PRP) to leucocyte- and plateletrich fibrin (L-PRF). Trends Biotechnol. Mar. 2009; 27(3):158-67.
Li PS et al A novel albumin-based tissue scaffold for autogenic tissue engineering applications Sci. Rep. Jul. 18, 2014;4:5600.
Chakrabarty, Subhas, Fibrin Solubilizing Properties of Certain Anionic and Cationic Detergents, Thrombosis Research, 1989, pp. 511-519, vol. 55.
Kolehmainen, Preparation of 3D Fibrin Scaffolds for Stem Cell Culture Applications, Journal of Visualized Experiments, Mar. 2012, pp. 1-4, vol. 61.

* cited by examiner

*Primary Examiner* — Taeyoon Kim
(74) *Attorney, Agent, or Firm* — Browdy and Neimark, PLLC

(57) ABSTRACT

The present invention provides methods for preparing modified blood clots comprising removal of the cellular content of the blood clots. The invention further provides uses of the modified blood clots as therapeutic agents and as delivery vehicles for cells, bio-molecules and other agents.

10 Claims, 11 Drawing Sheets

MODIFIED BLOOD CLOTS

TECHNOLOGICAL FIELD

This invention relates to the field of tissue healing and hemostasis. More specifically, it describes modified blood clots and their use as therapeutic agents and as delivery vehicles for cells and bio-molecules.

BACKGROUND ART

References considered to be relevant as background to the presently disclosed subject matter are listed below:
1. Gale A J. Current Understanding of Hemostasis. *Toxicologic pathology.* 2011; 39(1):273-280
2. Mosesson M W. Fibrinogen and fibrin structure and functions. *J Thromb Haemost.* 2005 August; 3(8):1894-904.
3. Dickneite G, Metzner H, Pfeifer T, Kroez M, Witzke G. A comparison of fibrin sealants in relation to their in vitro and in vivo properties. *Thromb Res.* 2003; 112(1-2):73-82.
4. WO1993005822
5. U.S. Pat. No. 7,125,569
6. WO2015128858
7. Blair P, Flaumenhaft R. Platelet α-granules: Basic biology and clinical correlates. *Blood reviews.* 2009; 23 (4): 177-189.
8. Dohan Ehrenfest D M, Rasmusson L, Albrektsson T. Classification of platelet concentrates: from pure platelet-rich plasma (P-PRP) to leucocyte- and platelet-rich fibrin (L-PRF). *Trends Biotechnol.* 2009 March; 27(3):158-67.
9. WO2010100570
10. Li P S et al A novel albumin-based tissue scaffold for autogenic tissue engineering applications *Sci. Rep.* 2014 Jul. 18; 4: 5600.

Acknowledgement of the above references herein is not to be inferred as meaning that these are in any way relevant to the patentability of the presently disclosed subject matter.

BACKGROUND

Hemostasis is the physiological process that stops bleeding at the site of an injury while maintaining normal blood flow elsewhere in the circulation. Blood loss is stopped by formation of a hemostatic plug (reviewed in Gale A J).

The process of hemostasis includes platelet aggregation, platelet plug formation and deposition of insoluble fibrin, which is generated by the proteolytic coagulation cascade. This insoluble fibrin forms a mesh that is incorporated into and around the platelet plug. This mesh serves to strengthen and stabilize the blood clot.

Various types of blood clot replacement products have been produced, for example fibrin sealants, also known as "fibrin glue" (see, for example, Dickneite G, et al).

A fibrin sealant is formed by enzymatic reactions involving fibrinogen, thrombin and Factor XIII. The thrombin converts the fibrinogen to fibrin by enzymatic action at a rate determined by the thrombin concentration. Factor XIII, an enzyme of the blood coagulation system, cross-links and stabilizes the fibrin clot. The fibrin formulation may further comprise anti-proteolytic agents (e.g. as described in WO1993005822). Plasminogen may be removed in order to stop or delay fibrinolysis (see for example U.S. Pat. No. 7,125,569).

The production process of fibrinogen fractions may result in the partial or complete removal of some of the plasma proteins from the fibrinogen composition. WO2015128858 discloses that supplementing a concentrated fibrinogen preparation with blood plasma results in a more stable fibrinogen formulation.

Another type of blood product is platelet concentrates (reviewed in Dohan Ehrenfest D M et al). Typically, the preparations are concentrates of viable platelets that are injected into a repair site in an inactivated state. Occasionally, an activator, such as calcium chloride or calcium gluconate, is added to the concentrate solution. Alternatively, such concentrate solutions are added to a scaffold, such as a collagen scaffold, which may result in some activation of the platelets in the concentrate solution.

General Description

The methods and compositions described herein relate in part to the surprising discovery that a blood clot (which is usually discarded as biological waste) can be modified, for example by eliminating the viable cells comprised in the clot, and administered to a patient in order to enhance therapeutic processes such as tissue regeneration and hemostasis. The cellular components of the clot, such as platelets (thrombocytes), white blood cells (WBCs, leukocytes) and red blood cells (RBCs, erythrocytes) are eliminated from the composition thereby a reusable clot with tissue regeneration properties is obtained.

The invention thus provides in a first of its aspects, a method for preparing a modified blood clot comprising:
  (a) Obtaining a blood clot; and
  (b) Removing the cellular content of said blood clot; thereby obtaining a modified blood clot.

In one embodiment, said blood clot is formed in vivo at a site of bleeding.

In one embodiment, the bleeding occurs during a surgical procedure, a traumatic injury or labor.

In one embodiment, said blood clot is formed ex vivo from a blood sample or a blood product obtained from a donor.

In one embodiment, the donor of the blood sample or blood product has a medical condition or a disease.

In one embodiment, the medical condition or disease is selected from the group consisting of an ischemic, degenerative, inflammatory, cancerous, genetic, traumatic, developmental or acquired medical condition or disease.

In one embodiment, said blood clot is formed ex vivo from a sample of umbilical cord blood, placental blood, peripheral blood, or pooled blood.

In one embodiment, said blood sample which is formed ex vivo is incubated in the absence of an anti coagulation agent.

In one embodiment, said blood sample which is formed ex vivo is incubated in the presence of at least one anticoagulant prior to clot formation.

In one embodiment, said at least one anticoagulant is selected from the group consisting of heparin, EDTA, citrate, oxalate, salts thereof, or combination thereof.

In one embodiment, following the incubation with the anticoagulant at least one agent capable of reversing the action of the anticoagulant is added to the blood sample.

In one embodiment, said at least one agent is calcium or a calcium salt.

In one embodiment, the blood sample is further incubated in the presence of a coagulation activator.

In one embodiment, said coagulation activator is a fibrinogen cleaving agent.

In one embodiment, said fibrinogen cleaving agent is thrombin.

In one embodiment, said step of removing the cellular content is performed by incubating the blood clot with at least one agent selected from the group consisting of a solubilizing agent, a detergent, a chelating agent, an enzyme, an antibody, a hypertonic solution, a hypotonic solution, a dehydrating agent, and any combination thereof.

In one embodiment, the method further comprises prior to step (a) a pre-modification step with a pre-modifying agent, wherein the pre-modifying agent is selected from a group consisting of a biomolecule, a drug, an antigen, a microbe, and a cell.

In one embodiment, said biomolecule is collagen or hyaluronic acid.

In one embodiment, said drug is an antibiotic drug or an anti-inflammatory drug.

In one embodiment, said antigen is a microbial antigen or a cancer cell antigen.

In one embodiment, said cell is a cancer cell or a blood cell.

In one embodiment, the method further comprises a processing step (c) after step (b), wherein the processing step is selected from the group consisting of dehydration, lyophilization, cryopreservation, partial or complete digestion, purification, solubilization, fractionation, lysis and any combination thereof.

In another embodiment, the method further comprises after step (b) a step (c) of seeding cells or cell aggregates onto the modified blood clot, and optionally a further step (d) of eliminating the cells or cell aggregates from the modified blood clot, thereby changing at least one biological and/or mechanical property of the modified blood clot.

In another aspect, the present invention provides a method of entrapping at least one agent within an insoluble biocompatible scaffold, said method comprising:
  (a) Obtaining a blood clot; and
  (b) Removing the cellular content of said blood clot;
thereby obtaining a modified blood clot wherein said modified blood clot is characterized by being insoluble, biocompatible and comprising at least one agent entrapped therein.

In one embodiment, the at least one agent is selected from the group consisting of soluble plasma molecules, activated platelet-derived molecules, and activated WBC-derived molecules.

In one embodiment, said at least one agent is albumin.

In another aspect, the present invention provides a modified blood clot prepared according to the methods disclosed herein.

In another aspect, the present invention provides a modified blood clot wherein said modified blood clot is modified ex vivo and is characterized by one or more of the following:
  (a) stabilized with anti-fibrinolytic factors,
  (b) free or substantially free of cellular content,
  (c) incorporates biomolecules with antimicrobial activity,
  (d) incorporates activated platelets and activated WBC-derived biomolecules,
  (e) incorporates platelets and WBC activating factors, and
  (f) incorporates soluble serum biomolecules such as albumin.

In one aspect, the modified blood clot of the invention is seeded ex vivo with cells or cell aggregates.

In one embodiment, said cells or cell aggregates are selected from the group consisting of differentiated cells, precursor cells, pluripotent cells or stem cells.

In another embodiment, said cells or cell aggregates are primary cells, cells from an established cell line, genetically modified cells or hormone-producing cells.

In one embodiment, said seeded cells or cell aggregates are eliminated from the modified blood clot, optionally prior to use of the modified blood clot.

In one embodiment, said modified blood clot is a disease-specific modified blood clot or a disease-stage specific modified blood clot.

In another aspect, the present invention provides a pharmaceutical composition comprising the modified blood clot of the invention and a pharmaceutically acceptable carrier or excipient.

In another aspect, the present invention provides a method of treating a disease or medical condition, said method comprising the step of administering the modified blood clot of the invention or the pharmaceutical composition of the invention to a subject in need thereof, wherein said disease or medical condition is selected from the group consisting of ischemic, degenerative, inflammatory, cancerous, genetic, traumatic, developmental or acquired medical condition or disease.

In one embodiment, said subject is a mammal.

In another embodiment, said subject is a human.

In another aspect, the present invention provides the modified blood clot of the invention for use in hemostasis, wound healing, soft tissue reconstruction and/or repair, graft adhesion, soft tissue filling, tissue regeneration, and for control of infections at surgical sites or in contaminated medical settings.

In another embodiment, the present invention provides the modified blood clot of the invention for use as a scaffold for tissue regeneration.

In another embodiment, the present invention provides the modified blood clot of the invention for use in cell delivery into a subject in need thereof.

In another embodiment, the present invention provides the modified blood clot of the invention for use in providing a supportive microenvironment for cell growth, differentiation and/or delivery into a subject in need thereof.

In another embodiment, the present invention provides the modified blood clot of the invention for use in drug delivery into a subject in need thereof.

In another aspect, the present invention provides use of the modified blood clot of the invention in the preparation of a pharmaceutical composition for hemostasis, wound healing, soft tissue reconstruction and/or repair, graft adhesion, soft tissue filling, tissue regeneration, and for control of infections at surgical sites or in contaminated medical settings.

In another aspect, the present invention provides a method of changing cells, multi-cellular aggregates or tissues comprising a step of exposing said cells, multi-cellular aggregates or tissues to the modified blood clot of the invention.

In another aspect, the present invention provides a kit comprising:
  (a) A container comprising the modified blood clot of the invention or the pharmaceutical composition of the invention; and
  (b) Instructions for use of the kit.

In one embodiment, the kit further comprises a container comprising at least one coagulation activator.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
FIG. 1 is a macroscopic view of spontaneously forming blood clots treated with different chemical compounds: sodium dodecyl sulfate (FIG. 1A) and RBC lysis buffer (FIG. 1B).

For the purposes of promoting an understanding of the principles of the invention, reference will now be made to preferred embodiments and specific language will be used to describe the same. It will nevertheless be understood that no limitation of the scope of the invention is thereby intended. Rather, such alterations and further modifications of the invention, and such further applications of the principles of the invention as illustrated herein, as would be contemplated by one having skill in the art to which the invention relates are intended to be part of the present invention.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Disclosed herein are modified blood clot (MBC) compositions, methods of manufacture and methods of use.

The method of preparing the modified blood clot disclosed in the present invention is based on the normal coagulation process and does not merely mimic its last phase (such as in the case of fibrin sealants). As a result, and without wishing to be bound by theory, this highly regulated process yields a multi-functional scaffold having a structure and biological activities which are highly similar to those present in the clot in-vivo.

In some of the aspects, as will be elaborated further below, the MBC is devoid of cells hence it can be used off-the-shelf for allogeneic therapy.

Moreover, it can be stored under conditions suitable for non-cellular compositions, for example it can be stored freeze-dried and at room temperature, acquiring long shelf life.

The MBC incorporates otherwise soluble, various serum biomolecules, such as serum albumin, acquiring the biological activities of such albumin to the MBC.

Furthermore, the MBC is enriched with biomolecules having profound antimicrobial activity, such as for example WBC-activating factors, WCB-derived antimicrobial biomolecules, immunoglobulins and complement subunits. The composition can thus be used in contaminated medical settings, and for control of infections at surgical sites.

The preparation of the MBC of the invention is relatively simple, thus reducing the time and costs associated with manufacturing. Similarly, the MBC are easy to use and convenient to prepare by the practitioner (the end-user), i.e. the MBC as an end-product does not contain multiple components and hence no assembly step is required by the practitioner.

The physical properties of the MBC such as its 3D shape, viscoelasticity, porosity, strength, stability and resistance to fibrinolysis can be tightly controlled.

The characteristics of the MBC render it a safe and efficient autologous or allogeneic means for delivery of various therapeutic agents, such as cells or drugs.

Therefore, the present invention provides in a first of its aspects a method for preparing a modified blood clot (MBC) comprising:
 (a) Obtaining a blood clot; and
 (b) Removing the cellular content of said blood clot;
  thereby obtaining a modified blood clot.

Blood clots naturally form in the process of hemostasis. Hemostasis is the physiological process that stops bleeding at the site of an injury while maintaining normal blood flow elsewhere in the circulation. Blood loss is stopped by formation of a hemostatic plug (reviewed in Gale A J). There are two main components of hemostasis. Primary hemostasis refers to platelet aggregation and platelet plug formation. Platelets are activated in a multifaceted process, and as a result they adhere to the site of injury and to each other, plugging the injury. Platelet aggregation at the site of injury is mediated by platelet receptors (such as glycoprotein receptors), platelet-derived agonists (such as ADP, TXA2 and serotonin), platelet-derived adhesive proteins (such as vWF, vitronectin, P-selectin and CD40) and plasma-derived adhesive proteins (such as vWF, fibrinogen and fibronectin). Secondary hemostasis refers to the deposition of insoluble fibrin, which is generated by the proteolytic coagulation cascade. This insoluble fibrin forms a mesh that is incorporated into and around the platelet plug. This mesh serves to strengthen and stabilize the blood clot. These two processes happen simultaneously and are tightly regulated and mechanistically intertwined.

According to the invention, any type of blood clot can be used for the preparation of the modified blood clot. For example, the blood clot may be a spontaneously-forming clot, namely a clot formed under a spontaneous coagulation process, or a clot induced by coagulation factors or coagulation activators (also termed platelet activating agents), such as, but not limited to, thrombin.

According to the invention, the blood clot may be formed in-vivo, or ex-vivo.

In order to form a blood clot ex-vivo, blood or blood components are obtained. As used herein the term "blood or blood components" also termed herein "blood" or "blood product" or "blood sample" refers to any product or substance that is blood or is derived from blood. For example, blood products include, but are not limited to, whole blood (unfractionated blood), or blood fractions such as platelet mixtures, plasma, plasma enriched with platelets, e.g. platelet rich plasma, serum, serum albumin preparations, blood components and therapeutic protein compositions containing proteins derived from blood, and artificial preparations of the same, such as recombinant plasma.

"Plasma" and "blood plasma" may be used interchangeably and refer to the plasma fraction of blood that contains, inter alia, salts, enzymes, immunoglobulins (antibodies), clotting factors and proteins including albumin, factor VIII and fibrinogen. A "plasma source" may be plasma from fractionation, pooled plasma, cryo-poor plasma, recovered plasma, and the fluid portion of human blood collected by plasmapheresis. In one embodiment the plasma is thrombin depleted and/or factor depleted plasma.

The term "platelet mixture" refers to one type of blood product wherein the cellular element is primarily or only platelets. A platelet concentrate is one type of platelet mixture where the platelets are associated with a smaller than normal portion of plasma.

The term "platelet rich plasma" (PRP) typically relates to an ex vivo preparation consisting of platelets concentrated in a limited volume of plasma. In one embodiment the plasma is thrombin free and/or Factor depleted plasma. "Factor depleted plasma" relates herein to plasma depleted in one or more coagulation factors such as Factor II, Factor X, or Factor V.

"Factor-II depleted plasma" or "Factor II Deficient Plasma" or "Prothrombin Deficient Plasma" is manufactured from pooled normal human plasma depleted of Factor II or Prothrombin. The remaining activity of prothrombin may be e.g. less than or equal to, 10% or less than or equal to 1%.

The term "thrombin free plasma" relates to a plasma having activity of thrombin e.g. of equal to or less than 2 IU/ml or undetectable according to a clotting time assay or chromogenic assay.

The blood clot can be prepared ex-vivo by any means known in the art, such as for example recalcification of anticoagulated blood, spontaneous clotting of non-anticoagulated blood, or clotting induced or initiated by exogenous coagulation factors.

The blood or the blood components may be obtained from a patient's peripheral blood system, or from a placenta or from an umbilical cord.

The source of the blood clot may be autologous, allogeneic or xenogeneic.

The term "autologous" means derived from the same individual or involving one individual as both donor and recipient.

The term "allogeneic" means derived from a separate individual of the same species.

The term "xenogeneic" means derived from a separate species.

The coagulation can be initiated at a chosen point of time which is determined by the practitioner to be optimal for the method. An anti-coagulation agent (also termed herein anti-coagulant) may be added to the blood sample or blood product and thereby delay clot formation until a coagulation activator agent is added to allow the clot to form.

Representative examples of anticoagulants that may be suitable for use in the present invention include heparin, citrate, oxalates, ethylenediaminetetraacetic acid (EDTA) and salts thereof such as the dipotassium salt, a combination of citrate, theophylline, adenosine and dipyridamole (known as CTAD), sodium polyanethol sulfonate, and acid citrate dextrose and mixtures thereof. Broadly, the anticoagulant is present in an amount effective to inhibit blood coagulation. This amount generally ranges from a concentration of about 1 mM to about 200 mM, and in some other embodiments, from about 10 mM to about 50 mM, relative to volume of the blood or blood product sample.

In another embodiment of the invention, the coagulation is initiated when the blood or blood products is brought in contact with a coagulation activator. In another embodiment, the coagulation activator is a fibrinogen cleaving agent. In another embodiment of the invention, the coagulation is initiated by exposing the blood to an object, such as a glass bead.

As used herein, the term "platelet activating agent" or "platelet activator" refers to an agent that stimulates platelets to release factors stored in their granules, such as factors involved in the coagulation cascade, and to secrete cytokines involved in wound healing and inflammation. Platelet activating agents include, but are not limited to collagen, thrombin, ADP, a negatively charged surface (e.g., glass), serotonin, acetylcholine and combinations thereof.

The fibrinogen molecule is composed of two sets of alpha, beta and gamma chains joined together. Fibrinogen is converted to insoluble fibrin by thrombin. Fibrin assembly is initiated by thrombin-mediated release of fibrinopeptides termed Fp(A) and Fp(B) from the alpha and beta chains, respectively. This exposes polymerization sites that cause fibrin molecules to align and form double-stranded fibrils which undergo further association to create multi-stranded fibers.

Fibrinogen/fibrin has multiple biological functions mediated by multiple molecular and cellular interactions, including growth factor binding, leukocyte binding, interaction with the extracellular matrix by binding to fibronectin, mediation of platelet and endothelial cell attachment and spreading, fibroblast proliferation and promotion of capillary tube formation and angiogenesis.

"Fibrinogen cleaving agent" as used herein, means an enzyme capable of cleaving either fibrinopeptide A or fibrinopeptide B or both from fibrinogen. Commonly used fibrinogen-cleaving agents are thrombin, which may be obtained from any suitable source such as e.g. human or bovine, enzymes from snake venom such as e.g. batroxobin, calobin, fibrozyme, and enzymes from the venom of Bothrops jararacussu.

"Thrombin" or "thrombin polypeptide" is a mammalian serine protease which results from the cleavage of prothrombin (Factor II), a zymogen precursor, by another serine protease (Factor Xa). Thrombin is part of the blood coagulation cascade and converts fibrinogen into insoluble strands of fibrin, as well as catalyzes other coagulation-related reactions. In humans, prothrombin is encoded by the F2 gene, and the resulting polypeptide is proteolytically cleaved in the coagulation cascade to form thrombin.

Spontaneously-forming clots can be retrieved and used for the preparation of the MBC of the invention. Such spontaneously-forming blood clots, which are commonly considered as biological waste and are discarded, can be retrieved for example during surgical procedures, traumatic injuries and labors.

In another embodiment, blood can be obtained from a blood recovery system or a cell salvage machine (such as haemonetics Cell Saver).

In one embodiment, blood is obtained from a single donor. In another embodiment, multiple blood samples are obtained from multiple donors and are pooled.

In one embodiment, once obtained, the blood can be immediately used to form the MBC. In another embodiment the blood is stored or banked for future use.

The source (e.g. the donor) of the blood or blood product can be an animal, e g a mammal, or a human. The donor can be a living donor or a deceased donor, namely a cadaveric donor.

In one embodiment, the donor of the blood is a healthy individual. In another embodiment, the donor of the blood or blood product may have a medical condition or disease.

The major cellular components of a blood clot are platelets. Platelets store and secrete a variety of growth factors and cytokines that play critical role in healing processes, including, for example: platelet-derived growth factor, platelet activating factor, transforming growth factor-beta, insulin-like growth factor 1, epidermal growth factor, basic fibroblast growth factor, and vascular endothelial growth factor. These secreted factors also include chemotactic factors that can attract other healing factors to the site of injury (reviewed in Blair P and Flaumenhaft R).

In accordance with this aspect of the invention the method comprises a step of removing the cellular content of the blood clot. As used herein the term "removing the cellular content" refers to various means employed to achieve a blood clot that is substantially free of viable cellular components. "Substantially free", and its grammatical equivalents, refers to the qualitative condition of exhibiting total or near-total extent or degree of a characteristic or property of interest. Specifically, in the context of the present invention "substantially free" indicates that upon removal of the cells using the means that would be elaborated below, no cells or a negligible number of cells remain in the blood clot.

The terms "modified blood clot (MBC)" and "MBC composition" are used interchangeably herein. As used herein the term "modified blood clot" refers to a clot that was treated so as to remove platelets and other cellular content. The modified blood clot is a decellularized, three-dimensional scaffold incorporating various biomolecules derived from plasma, activated platelets, and activated WBCs that populated the blood clot prior to its modification.

As used herein, the term "activated" means that a cell or platelet has acquired one or more functional or phenotypic characteristics of an activated cell or platelet.

The blood clot modification, namely the step of removing the cellular content can be done by any mechanical, physical, chemical or biological means, substances or compounds known in the art. In general the methods employ a variety of mechanical, physical, chemical or biological means to disrupt, degrade, neutralize and/or destroy platelets and cellular content and/or facilitate removal of the platelets and cellular content. Such methods are disclosed in the art. The present invention is not limited to these techniques but also includes modifications of these techniques, as well as other techniques currently available or developed in the future.

In certain embodiments the blood clot is incubated with a modification agent or substance.

In one embodiment, the modification agent enhances cell lysis and destruction of cellular components, i.e. it disrupts and/or degrades cellular constituents such as cell membranes, proteins, nucleic acids, etc.

Modification may be accomplished using a single modification agent, or two or more modification agents.

In certain embodiments the modification agent is a solubilizing agent, a detergent, a chelating agent, an emulsifying agent, an enzyme, an antibody, a hypertonic solution, a hypotonic solution, a dehydrating agent, and any combination thereof.

Non limiting examples of suitable detergents include ionic detergents, e.g. SDS (sodium dodecyl sulfate), and nonionic detergents, e.g. Triton X (tert-octylphenylpolyoxyethylene), or a combination thereof.

In one embodiment, the modification agent solution comprises one or more of Triton X, CHAPS (3-[(3-cholamidopropyl)-dimethyl-ammonio]-1-propanesulfonate), or SDS in phosphate buffered saline (PBS). Other suitable detergents include polyoxyethylene (20) sorbitan mono-oleate and polyoxyethylene (80) sorbitan mono-oleate (Tween 20 and 80), sodium deoxycholate, and octyl-glucoside.

In certain embodiments the modification agent is a hypertonic solution (e.g. 3M NaCl) or a hypotonic solution (e.g. water or RBC lysis buffer). Aqueous hypotonic or low ionic strength solutions facilitate cell lysis through osmotic effects. Such solutions may comprise deionized water or an aqueous hypotonic buffer (e.g., at a pH of approximately 5.5 to 8, preferably approximately 7 to 7.5). In certain embodiments, the blood clot is modified with alternating hypertonic and hypotonic solutions.

The modification of the blood clot may cause residual damage to the extracellular matrix, due to proteases that are released upon lysis of the cells. Therefore, in certain embodiments of the invention various additives such as metal ion chelators, e.g., EDTA (ethylenediaminetetraacetic acid) and/or protease inhibitors are included in the solution. Suitable protease inhibitors include, for example, one or more of phenylmethylsulfonyl-fluoride (PMSF), aprotinin, leupeptin, and N-ethylmaleimide (NEM).

The modification solution may further include various enzymes that degrade cellular components. Such enzymes include nucleases (e.g., DNAses such as DNAse I, RNAses such as RNAse A), phospholipases (e.g., phospholipase A or C), and proteases (e.g. dispase II, trypsin, and thermolysin).

The activity of proteases is a function of time, temperature, and concentration, and these variables may be appropriately adjusted to achieve acceptable modification without unacceptable destruction of the extracellular matrix and the incorporated biomolecules. Nucleases are typically employed at a concentration of between 0.1 µg/ml and 50 µg/ml. Preferably, DNAse I is used at a concentration of about 10 µg/ml and RNAse A is used at a concentration of about 1.0 µg/ml for. The nucleases are preferably employed in a physiologically buffered solution at a temperature of between about 20° C. to 38° C., preferably 37° C.

The modification solution typically includes a buffer. Suitable buffers include organic buffers such as Tris (hydroxymethyl)aminomethane (TRIS), (N-[2-hydroxyethyl] piperazine-N'-[2-ethanesulfonic acid] (HEPES), and the like. Buffers including sodium phosphate, citrate, bicarbonate, acetate, or glutamate may also be used. In general, a pH between about 5.5 and 8.0, between about 6.0 and 7.8, or between about 7.0 and 7.5 is employed.

The examples of modification techniques provided above are not intended to be limiting, and the invention encompasses the use of essentially any cell removal technique.

The period of incubation of the blood clot with the modification compound or substance may vary and depends on the type of compound used, the temperature of the reaction (e.g. room temperature (e.g. about 20° C.), 37° C. or 4° C.) and on the size of the blood clot. In certain embodiments the incubation with the modification compound or substance is performed for from about 10 seconds to about one minute, from about 1 minute to about 30 minutes, e.g. 1 minute or 5 minutes or 10 minutes or 15 minutes or 20 minutes or 30 minutes, or 40 minutes or 50 minutes, or from 1 hour to 24 hours, or for one day, or two days, or three days, or four days, or five days, or six days, or 7 days, or 8 days or 9 days or 10 days or more.

The blood clot modification may cause damage to the remaining extracellular matrix, due to proteases that are released upon removal of cellular content. Therefore, in certain embodiments of the invention various additives such as metal ion chelators, e.g., EDTA and/or protease inhibitors are used.

The MBC composition of the invention can be further processed. For example, it can be fractionalized, lysed, purified, undergo complete or partial enzymatic digestion, solubilized, dehydrated, lyophilized, cryopreserved, or any combination of thereof.

The conditions of the blood clot modification process can be monitored, automated and controlled by a control system to achieve optimal results. The control system may be operated and controlled manually or automatically. The control system monitors parameters such as pressure, flow rate, temperature, pH level, oxygen levels, electrolyte levels, time duration and the like.

The effects of the modification on the blood clot architecture, content, mechanical and biological properties can be evaluated by any method which is known in the art. Examples of such methods include light and electron microscopy, histology, molecular biology assays, mass spectrometry, rheological and tensile tests and more.

The MBC composition can be administered to a subject immediately upon its preparation, or stored or banked for future use.

The modified blood clot (MBC) and the compositions comprising the MBC incorporate factors derived from a well-balanced number of activated platelets and activated WBC (i.e. the number normally found in blood blots, wherein platelets and WBC are associated with a normal portion of plasma). Such factors are efficiently entrapped within the composition and can be efficiently delivered to a subject.

Activated platelets are known to release granules containing various factors involved in coagulation, healing and regenerative processes. The methods of the current invention utilize the orchestrated release of these factors, and allow their effective entrapment in the MBC and their effective delivery into a subject.

WBC are involved in many healing processes, and in host defense response to foreign antigens and microbes. The common types of WBC include lymphocytes (such as T-cells, B-cells and natural killer cells), granulocytes (such as neutrophils, basophils and eosinophils) and monocytes (that differentiate into macrophages). The participation of WBC in healing processes and defense mechanisms is largely associated with their production of biomolecules such as immunoglobulins, cytokines and growth factors.

WBC can be activated, for example by incubation for a period of time and temperature allowing them to become activated, as disclosed for example in WO2010100570.

The blood or blood product used for the composition of the invention may contain WBC or may be mixed with WBC. WBC, either included in the blood product or added to the blood product may be activated. Thus, biomolecules produced by WBC or activated WBC can be effectively entrapped in the composition, and can be effectively delivered to a patient.

The present invention thus provides in another one of its aspects a modified blood clot wherein said modified blood clot is modified ex vivo and is characterized by one or more of the following:
  (a) It is stabilized with anti-fibrinolytic factors,
  (b) It is free or substantially free of cellular content,
  (c) It incorporates biomolecules having antimicrobial activity,
  (d) It incorporates activated platelets and activated WBC-derived biomolecules,
  (e) It incorporates platelets and WBC activating factors, and
  (f) It incorporates soluble serum biomolecules such as albumin.

As used herein the term "antimicrobial activity" refers to the ability to modify a function or metabolic process of a target microorganism, for example so as to at least partially affect replication, vegetative growth, toxin production, survival, viability in a quiescent state, or other attribute. In one embodiment, the term relates to inhibition of growth of a microorganism. In a particular embodiment, antimicrobial activity relates to the ability to kill at least one bacterial species. In another embodiment, the term can be manifested as microbicidal or microbistatic inhibition of microbial growth.

The term "microorganism" or "microbe" herein refers broadly to bacteria, fungi, viruses, and protozoa. In particular, the term is applicable for a microorganism having a cellular or structural component of a lipid bilayer membrane. In specific embodiments, the membrane is a cytoplasmic membrane. Pathogenic bacteria, fungi, viruses, and protozoa as known in the art are generally encompassed.

Antimicrobial activity of the MBC can be measured, for example, using a bacterial kill Assay. Briefly, a clinically relevant bacterium is placed in a sterile tube containing 4 ml of soy broth and grown overnight at 37° C. On day 2 of the experiment, a bacterial sample is serially diluted and treated with the MBC composition. The treated cultures are incubated at 37° C. overnight. On day 3, the bacterial cultures are placed on an agar plate and incubated for 24 hr at 37° C. The next day, the number of colonies formed is counted, and the antimicrobial effect of the MBC thus determined.

Examples of biomolecules with antimicrobial activity include Eosinophil peroxidase, mediating bacterial fragmentation and lysis, Eosinophil cationic protein, a cytotoxin and helminthotoxin, exhibiting gram-negative and gram-positive antibacterial activity, Neutrophil defensin 1, having antibacterial, fungicide and antiviral activities, Bactericidal permeability-increasing protein, an endogenous antibiotic protein with potent killing activity against Gram-negative bacteria, and Azurocidin, a neutrophil granule-derived antibacterial and monocyte- and fibroblast-specific chemotactic glycoprotein.

As used herein the term "biomolecule" refers to any molecule that is part of a living organism, or analogs thereof, that engages in a biological activity or which is effective in modulating a biological activity such as eliminating, reducing or enhancing various biological reactions. Thus, biomolecules include for example amino acids, or polymers of amino acids, such as peptides and proteins (including antibodies and enzymes), lipids, such as fatty acids, glycolipids, sterols, glycerolipids and phospholipids, nucleosides and nucleotides, nucleic acids or polymers of nucleic acids such as RNA or DNA molecules, carbohydrates, such as monosaccharides, disaccharides and polysaccharides, vitamins, hormones, neurotransmitters, metabolites, antibodies, enzymes and synthetically produced analogs of the above.

Examples of biomolecules that stabilize the MBC include Factor XIII, a coagulation factor that cross-links fibrin, thus stabilizing the fibrin clot, and Alpha-2-antiplasmin, a protease inhibitor that inactivates pepsin and contributes to resistance to fibrinolysis.

As used herein the term "substantially free" as it relates to the cellular content of the modified blood clot means that upon removal of the cells using the means described above no cells or a negligible number of cells remain in the blood clot.

In one embodiment the MBC comprises at least one protein from the proteins listed in Table 1. In other embodiments the MBC comprises at least 85%, or 90%, or 95%, or 98%, or 99% or all of the proteins listed in Table 1. In one embodiment the MBC consists of at least 85%, or 90%, or 95%, or 98%, or 99% or all of the proteins listed in Table 1.

In one embodiment the MBC comprises at least one pathway from the pathways listed in Table 2. In other embodiments the MBC comprises at least 85%, or 90%, or 95%, or 98%, or 99% or all of the pathways listed in Table 2. In one embodiment the MBC consists of at least 85%, or 90%, or 95%, or 98%, or 99% or all of the pathways listed in Table 2. In a preferred embodiment the MBC comprises at least one of the following proteins: PRG2 proteoglycan 2; EGF-containing fibulin-like extracellular matrix protein 1; Transforming growth factor-beta-induced protein ig-h3 (TGFBI); Alpha-2-antiplasmin; Thrombospondin 1 (TSP-1); platelet-related factors, such as compounds present in alpha granules content: vWF, CLCX7 (platelet basic protein, a chemokine), fibronectin, fibrinogen, thrombospondin, Transforming growth factor beta-1 (TGF-β1); CD36; proteins associated with vesicular trafficking and maturation: e.g. Clathrin, AFR3, NSFL1 cofactor p47, AP-1 complex subunit beta-1, AP-2 complex subunit alpha-1, Ras-related protein Rab-5B or Talin.

The protein PRG2 proteoglycan 2 is the predominant constituent of the crystalline core of the eosinophil granule. High levels of the proform of this protein are also present in placenta and pregnancy serum, where it exists as a complex with several other proteins including pregnancy-associated plasma protein A (PAPPA), angiotensinogen (AGT), and C3dg. This protein may be involved in antiparasitic defense mechanisms as a cytotoxin and helminthotoxin, and in immune hypersensitivity reactions. The encoded protein contains a peptide that displays potent antimicrobial activity against Gram-positive bacteria, Gram-negative bacteria, and fungi. It is directly implicated in epithelial cell damage, exfoliation, and bronchospasm in allergic diseases. Alternatively spliced transcript variants encoding different isoforms have been found for this gene.

The protein EGF-containing fibulin-like extracellular matrix protein 1 binds EGFR, the EGF receptor, inducing EGFR autophosphorylation and the activation of downstream signaling pathways. It may play a role in cell adhesion and migration.

Transforming growth factor-beta-induced protein ig-h3 (TGFBI): This protein is induced by TGF-β, it binds to type I, II, and IV collagens. This adhesion protein may play an important role in cell-collagen interactions.

Alpha-2-antiplasmin: This protein is a protease inhibitor that inactivates pepsin and contributes to resistance to fibrinolysis.

Thrombospondin 1 is an adhesive glycoprotein that mediates cell-to-cell and cell-to-matrix interactions. This protein can bind to fibrinogen, fibronectin, laminin, type V collagen and integrins and has been used as a marker of platelet activation.

CD36 is a platelet surface glycoprotein. It is a cell adhesion molecule which binds to collagen and thrombospondin. Latent TGF-β complex is bound to CD36 via its ligand, thrombospondin-1 (TSP-1).

Talin is a master regulator of platelet integrin activation in vivo.

The MBC can be substantially free of plasmin and/or plasminogen. The removal of plasmin and plasminogen from the blood used to form the MBC can be carried out by any method described in the art.

The 3D (three dimensional) shape of the MBC composition can be controlled. Prior to the formation of insoluble fibrin, the blood or blood products are normally liquid or pliable. Using a frame or a mold, the blood or blood product can be shaped into any desired 3D form or appearance. Once the assembly is complete, the blood clot acquires a modified shape. Then, the blood clot is modified to form the composition of the invention with any desired 3D shape. Non limiting examples of blood clots having various 3D shapes are shown in FIG. 3.

The mechanical properties of the MBC composition can be modified. For example, prior to blood clot modification, the blood clot can be subject to mechanical stimuli, such as tensile force, and acquire modified mechanical properties. Then, the blood clot is treated to form the MBC composition of the invention.

In one embodiment, the MBC composition is flexible, namely the MBC can withstand applied stress during normal use without rupturing. Due to the flexibility of the MBC composition, it conforms to most continuous contours whereto it is applied.

According to the present invention, the blood or blood product can be pre-modified, namely it may be exposed prior to clotting to one or more pre-modifying agents.

Pre-modification encompasses, for example, incorporation of additional biomolecules or elimination of existing biomolecules. In one embodiment, pre-modification may mean activation of platelets or WBC.

Pre-modifying agents may include biomolecules, drugs, microparticles, nanoparticles, imaging agents, antigens, microbes and cells.

"Microparticle" and "nanoparticle" refer to a polymeric particle of microscopic and nanoscopic size, respectively, optionally containing a drug or an agent dissolved, dispersed, entrapped, encapsulated, or attached thereto.

The term "particle" refers to a small object, fragment, or piece of material and includes, without limitation, polymeric particles, biodegradable particles, nonbiodegradable particles, single-emulsion particles, double-emulsion particles, coacervates, liposomes, microparticles, nanoparticles, macroscopic particles, pellets, crystals, aggregates, composites, pulverized, milled or otherwise disrupted matrices, cross-linked protein or polysaccharide particles. Particles may be composed of a single substance or multiple substances.

Non-limiting examples of biomolecules include collagen and hyaluronic acid.

Non-limiting examples of drugs include antibiotic drugs and anti-inflammatory drugs.

As used herein the term "antigen" refers to any substance that may be specifically bound by an antibody molecule. Thus, the term antigen encompasses biologic molecules including, but not limited to, simple intermediary metabolites, sugars, lipids, and hormones, as well as macromolecules such as complex carbohydrates, phospholipids, nucleic acids and proteins.

Non-limiting examples of antigens include microbial antigens and cancer cell antigens Non-limiting examples of cells include cancer cells or blood cells.

The pre-modifying cells may be activated or non-activated cells, adherent or non-adherent cells.

The MBC of the invention can be used as a novel form of a scaffold for tissue engineering applications as are known in the art. The composition can be used as raw material for scaffold fabrication by any means known in the art. In one embodiment, the MBC composition is a scaffold for cell implantation and cell delivery. In another embodiment, the MBC composition is a scaffold for drug delivery.

The MBC composition can be combined with drugs, biologics (such as biomolecules, cells and tissues) and medical devices.

The composition can be used as a reservoir of plasma molecules, which can be harvested or isolated from the composition upon a need.

As indicated above the MBC may be prepared from a patient suffering from a medical condition or disease.

The medical condition or disease is selected from one or more of the following: ischemic, degenerative, inflammatory, cancerous, genetic, traumatic, developmental or acquired medical condition or disease.

According to the present invention, the timing of obtaining blood from a patient is scheduled to be in accordance with a specific stage or degree of a medical condition or disease.

The blood may be obtained once or obtained multiple times.

Thus, according to the present invention disease-specific or disease stage-specific blood samples can be obtained. Furthermore, the MBC obtained from such blood samples are rendered disease-specific or disease stage-specific, respectively, and can be used to treat such specific disease or a stage of disease.

In one embodiment, the MBC is made to fit an acute stage of a disease or medical condition. In another embodiment, the MBC is made to fit a non-acute stage of a disease or medical condition, such as sub-acute or chronic stage.

In one embodiment, once obtained, the disease-specific or disease-stage specific blood can be immediately used to form the MBC. In another embodiment the disease-specific or disease-stage specific blood is stored or banked for future use.

Cells, multi-cellular aggregates or tissues can be affected or changed by exposure to the disease-specific or disease stage-specific MBC of the current invention. Therefore, another aspect of the present invention concerns a method of changing cells, multi-cellular aggregates or tissues by exposure to the MBC.

In one non limiting example the cells are stem cells.

Stem cell therapy has emerged as a promising therapeutic modality in a variety of medical fields, due to their self-renewal and differentiation capacities, as well as the ability to restore tissue homeostasis and regenerate diseased or injured tissues.

Yet, their clinical use is limited due to several reasons, such as low engraftment and survival rates at the host target site, immune rejection by the host immune system, and reduced functionality or non-significant therapeutic activity that may result from suboptimal culture conditions during ex-vivo expansion.

In an attempt to increase their therapeutic effectiveness cells may be preconditioned prior to use. In-vitro exposure to stresses that cells experience in damaged tissues, such as oxidative stresses, hypoxic culture conditions and heat shock treatment, can enhance stem cell survival in-vivo. In addition, cells may be exposed to molecules such as growth factors that may affect their differentiation state and improve their survival rates.

Furthermore, it has been postulated that upon transplantation stem cells encounter specific stimulating environments that activate them to produce specific therapeutic effects.

According to the present invention, cells, such as stem cells can be changed by exposure to the MBC, in a way that increases their therapeutic effectiveness, and more precisely adjust their ability to treat a medical condition or disease in a patient. As used herein the term "change" (or "alteration") encompasses one or more of the following: changes in biological properties, changes in functionality, changes in physical properties, changes in mechanical properties, changes in chemical properties, a stimulatory effect, an inhibitory effect, changes in architecture, changes in content, enhanced biocompatibility, enhanced engraftment, enhanced survival, enhanced homing, enhanced therapeutic effect, changes in adverse reactions or side effects, differentiation, changes in cellular phenotype, changes in immunological properties, or changes in immune-compatibility.

In order to facilitate the alteration of the cells by the MBC, the cells must come into contact with the MBC by any means known in the art. In a preferred embodiment, the cells come into contact with the MBC by seeding said cells on the MBC. In another embodiment, the cells are incubated with a culture medium supplemented with an effective amount of MBC.

In one embodiment, the cells come into contact with the MBC for a period of time sufficient to achieve the desired change.

In another embodiment the cells come into contact with the MBC for a short term, such as for example between 12 and 48 hours. In another embodiment the incubation time is longer, such as for example between 2 and 28 days.

In another embodiment, the composition to be affected by the MBC is an extract derived from stem cells. Such compositions are disclosed for example in WO/2009/098698.

In another embodiment, scaffolds and extract compositions such as disclosed in WO/2009/098698 can be changed by bringing the cells or tissues used to generate these scaffolds and extract compositions in contact with the MBC of the present invention.

In one embodiment, the MBC composition of the current invention may be re-seeded with cells and/or platelets, prior to administration to a subject.

The seeded cells may interact with the MBC and further modify the biological and mechanical properties of the MBC, e.g. to form an ECM upon the MBC and to secret various soluble factors, thereby supplementing the MBC with additional agents. In other words, the interaction of the seeded cells with the MBC results in redesigning of the MBC.

As used herein the term "redesigning" refers to the modification of the MBC by the seeded cells. This modification occurs at the structural and functional level and is a result of an interaction between the seeded cells and the MBC. Redesigning includes for example global reshaping of the architecture and integration of newly synthesized matrix elements. Redesigning may improve the physical and biological characteristics of the MBC, as well as the matching of the MBC to treat a specific target tissue or a specific patient, by seeding tissue-specific cells or by seeding cells which are autologous to a patient.

Redesigning can also be done by serially seeding several types of cells, or simultaneously by seeding a mixed population of several types of cells, followed by the elimination of the cells by any suitable technique.

The seeded cells may be further removed prior to administration of the MBC to a recipient. Redesigning may consist of one or more cycles of cell seeding and elimination, wherein one or more cell types are seeded onto the MBC simultaneously or sequentially.

In accordance with the invention, the seeded cells may be autologous, allogeneic or xenogeneic with respect to the host into which the composition is administered.

The cells can be obtained from any type of animal. In one embodiment, cells are isolated from mammals, such as monkeys, dogs, cats, mice, rats, cows, horses, pigs, goats and sheep.

In a preferred embodiment the cells are human cells.

The cell may be any cell type, including, for example, a differentiated cell, a precursor cell, or a stem cell. The cell may be a thrombocyte. The cell may be a pluripotent cell.

The cell may be a primary cells, a cell from established cell line, or genetically modified cell.

In a preferred embodiment, about 5,000 cells to 500 million cells are suspended in medium and applied to each square centimeter of a surface of a MBC. Preferably, between 50,000 and 50 million cells, and more preferably, between 50,000 and 5 million cells are suspended in media and applied to each square centimeter of a surface of a MBC. The MBC is incubated under standard culturing conditions, such as, for example, 37° C., 5% CO2, for a period of time until the cells attach. It will be appreciated that the density of cells seeded onto the MBC can be varied. Other seeding techniques may also be used depending on the cells. For example, the cells may be applied to the MBC by vacuum filtration. Selection of cell types, and seeding of cells onto a MBC, will be routine to one of ordinary skill in the art in light of the teachings herein.

In one embodiment, the MBC are seeded with one population of cells. In another embodiment, the MBC is seeded on two sides with two different populations of cells. This may be performed by first seeding one side of the MBC and then seeding on the other side. For example, the MBC may be placed with one side on top and seeded. Then the MBC may be repositioned so that a second side is on top. The second side may then be seeded with a second population of cells. Alternatively, both sides of the MBC may be seeded at the same time. For example, two cell chambers may be positioned on both sides (i.e., a sandwich) of the MBC. The two chambers may be filled with different cell populations to seed both sides of the MBC simultaneously. The sandwiched MBC may be rotated, or flipped frequently to allow equal attachment opportunity for both cell populations.

In another embodiment, two separate MBC are seeded with different cell populations. After seeding, the two MBC may be attached together to form a single unit with two different cell populations on the two sides. Attachment of the MBC to each other may be performed using standard procedures such as fibrin glue, liquid co-polymers, sutures and the like.

In order to facilitate cell growth on the MBC of the present invention, the MBC may be coated with one or more cell adhesion-enhancing agents. These agents include but are not limited collagen, laminin, and fibronectin.

In addition, the cells may be cultured onto the MBC in the presence of agents that promote cellular proliferation and growth. Such agents include a number of growth factors that can be selected based upon the cell types present (non limiting examples include: keratinocyte growth factor (KGF); vascular endothelial cell growth factor (VEGF); platelet derived growth factor (PDGF); fibroblast growth factor (FGF); transforming growth factor (TGF)α, β, and the like; insulin; growth hormone; colony stimulating factors; erythropoietin; epidermal growth factor (EGF); and hepatic erythropoietic factor (hepatopoietin)). Serum, such as fetal bovine serum (FBS) or the like, can also provide some of these growth factors. In addition, agents such as ascorbic acid can be used to increase extracellular matrix production.

In one embodiment, cells are substantially eliminated from the seeded MBC of the invention prior to further use to provide a cell-free MBC enriched and conditioned with extracellular matrix components and secreted factors provided by the population of seeded cells. A cell-free MBC may have a reduced level of immunogenicity, and may provide an appropriate matrix for host cell repopulation or secondary cell seeding.

Cell removal or elimination may be achieved by any suitable technique known in the art, for example the techniques described above for removal of the cellular content of the blood clot. Cells may be eliminated from the seeded MBC, for example by air-drying or lyophilization to kill the cells. Thermal shock, radiation, acoustic treatment, changes in pH, mechanical disruption, addition of toxins, detergents (SDS or triton ×100), enzymes (RNAase, DNAase, protease, lipase), or solvents (alcohol, acetone, or chloroform) may also be used. In addition, treatment with hypotonic or hypertonic solutions, which have non-physiological ionic strengths, can also promote the cell elimination process. See, for example, WO 9603093 and WO 9632905.

Essentially any cell can be used in the methods and compositions described herein.

The cells include at least one of cardioprogenitor cells, cardiac muscle cells; cardiac fibroblasts; endothelial cells; skeletal muscle cells; smooth muscle cells; endothelial progenitor cells; skeletal muscle progenitor cells; neuroprogenitor cells; nerve cells; dermal fibroblasts; ectodermal cells; bone cells; cartilage cells; tendon cells; ligament cells; hepatocytes; pancreatic islet cells; intestinal cells; progenitor cells derived from a tissue selected from the group consisting of bone marrow or fat; stem cells; induced pluripotent stem cells (iPS cells); hormone-producing cells, and genetically transformed cells.

As used herein, "Islet cell" refers to an endocrine cell derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogenous populations of these cells. In preferred embodiments, a population of islet cells contains at least beta cells.

As used herein, the term "stem cell" refers to a cell which is capable of self-renewal, i.e., proliferation to give rise to more stem cells, and may give rise to lineage committed cells, capable of differentiation into a lineage-specific cell type. The stem cell may be a totipotent, pluripotent, multipotent, oligopotent or unipotent stem cell. As used herein, the term "pluripotent cell" means a cell capable of differentiating into cells of all three germ layers. Examples of pluripotent cells include embryonic stem cells and induced pluripotent stem (iPS) cells. The stem cell may be a cell expressing one or more markers of multilineage differentiation potential, or a cell expressing one or more markers of pluripotent stem cells.

Where the cell is maintained under in vitro conditions, conventional tissue culture conditions and methods can be used, and are known to those of skill in the art. Isolation and culture methods for various cells are well within the knowledge of one skilled in the art.

Both heterogeneous and homogeneous cell populations are contemplated for use with the methods and compositions described herein. In addition, aggregates of cells, cells attached to or encapsulated within particles, cells within injectable delivery vehicles such as hydrogels, and cells attached to transplantable substrates including scaffolds are contemplated for use with the methods and compositions described herein.

A variety of means for administering cells to subjects are known to those of skill in the art. Such methods can include systemic injection, for example intravenous (i.v.) injection or implantation of cells into a target site in a subject. Other methods can include intratracheal delivery, intrathecal delivery, intraosseous delivery, pulmonary delivery, buccal delivery, and oral delivery. Cells can be inserted into a delivery device which facilitates introduction by injection or implantation into the subjects. Such delivery devices can include tubes, e.g., catheters, for injecting cells and fluids into the body of a recipient subject. In one preferred embodiment, the tubes additionally have a needle, e.g., a syringe, through which cells can be introduced into the subject at a desired location. In some embodiments, cryopreserved cells are thawed prior to administration to a subject.

The term "hydrogels" refers to 3-D networks of molecules typically covalently (e.g., polymeric hydrogels) or non-covalently (e.g., self-assembled hydrogels) held together where water is the major component (usually greater than 80%).

In some embodiments, the cells are contained within an organ, tissue, or cell aggregate (such as for example pancreatic islet, ovarian follicle) or a tissue-engineered analogue thereof.

The MBC can also serve as a scaffold for cell delivery, providing a microenvironment for the cells.

As used herein, "scaffold" refers to a structure that provides a surface suitable for adherence and proliferation of cells. A scaffold may further provide mechanical stability and support. A scaffold may be in a particular shape or form so as to influence or delimit a three-dimensional shape or form assumed by a population of proliferating cells.

The transplantation of hormone- or protein-secreting cells into a subject in need is a promising strategy for the treatment of many diseases, disorders and medical conditions.

There is a need in the art for a biocompatible material that can be combined with cells intended for delivery into a subject, while providing some important cell-ECM cues essential for cell viability, growth and function. Essentially, there is a need for a biocompatible material that can provide microenvironment for the cells. The term "microenvironment" refers to an environment that comprises molecules that come in contact with the cells and may be influenced by the cells, such as cell-ECM cues essential for cell viability, growth and function. It also refers to chemical and physical parameters surrounding the cells, such as for example pH, ionic strength, 3D architecture and porosity, In a preferred embodiment, cells or cell aggregates are combined or mixed with the MBC of the invention to create an MBC-cells composition.

The MBC-cells composition may be formed by any method know in the art. A preferred method is encapsulation.

Methods and composition for encapsulating cells are known in the art. See for example WO2014153126.

As used in the present invention the term "encapsulation" means to entrap cells within the boundaries of a biocompatible material.

The MBC may serve as a microcapsule. As used herein, the term "microcapsule" refers to a MBC or MBC fragment having a mean diameter of about 150 µm to about 1000 µm. The MBC microcapsule may have any shape suitable for cell encapsulation. The MBC microcapsule may contain one or more cells dispersed therein, thereby "encapsulating" the cells.

In a preferred embodiment, MBC capsules or microcapsules are fabricated from a solution of MBC containing suspended cells using the encapsulator (such as an Inotech encapsulator).

In preferred embodiments, the MBC containing cells is washed with, for example, HEPES solution, Krebs solution, and/or RPMI-1640 medium.

Cells can be obtained directly from a donor, from cell culture of cells from a donor, or from established cell culture lines. In the preferred embodiments, cells are obtained directly from a donor, washed and implanted (seeded) directly onto the MBC. The cells are cultured using techniques known to those skilled in the art of tissue culture. In the preferred embodiment, the cells are autologous—i.e., derived from the individual into which the cells are to be transplanted, but may be allogeneic or heterologous.

Cell attachment and viability can be assessed using scanning electron microscopy, histology, and quantitative assessment with radioisotopes. The functionality or viability of the implanted cells can be determined using a combination of the above-techniques and functional assays.

The MBC of the invention can be used to deliver a single cell type, multi-cellular aggregates (such as pancreatic islets and ovarian follicles or tissue-engineered analogues thereof), multiple cell types, including genetically altered cells, within their three-dimensional scaffolding for the efficient transfer of large numbers of cells and the promotion of transplant engraftment for the purpose of creating a new tissue or tissue equivalent. It can also be used for immune-protection of cell transplants while a new tissue or tissue equivalent is growing by excluding the host immune system.

Examples of cells which can be implanted as described herein include stem cells, platelets, chondrocytes and other cells that form cartilage, osteoblasts and other cells that form bone, muscle cells, fibroblasts, keratinocytes, oocytes, germ cells, ovarian cells and organ cells. As used herein, "organ cells" includes hepatocytes, islet cells, cells of intestinal origin, cells derived from the kidney, and other cells acting primarily to synthesize and secret, or to metabolize materials or biomolecules. A preferred cell type is an insulin-producing cell.

The MBC can be combined with humoral factors to promote cell transplantation and engraftment. For example, the MBC can be combined with angiogenic factors, antibiotics, anti-inflammatory factors, growth factors, compounds which induce differentiation, and other factors which are known to those skilled in the art of cell culture.

For example, humoral factors could be mixed in a slow-release form with the cell-MBC composition prior to transplantation. Alternatively, the MBC could be modified to bind humoral factors or signal recognition sequences prior to combination with cells.

The techniques described herein can be used for delivery of many different cell types to achieve different tissue structures. In the preferred embodiment, the cells are mixed with the MBC and injected directly into a site where it is desired to implant the cells. However, the MBC may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space.

The MBC-cells composition can be transplanted into a patient in need thereof to treat a disease or disorder. In some embodiments, the cells are obtained from a genetically non-identical member of the same species. In alternative embodiments, the cells are obtained from a different species than the patient. In preferred embodiments, hormone- or protein-secreting cells are combined with the MBC and transplanted into a patient to treat a disease or disorder. In preferred embodiments, the disease or disorder is caused by or involves the malfunction hormone- or protein-secreting cells in a patient.

The MBC-cells composition may be included in a solution together with any other component or the MBC-cells composition may be kept in a separate solution. This may be determined depending on the origin of the cells and the selection of the best environment for viable cells. If cells are cultured the cells may be provided suspended in cell growth media, alternatively cells may be suspended in other suitable solutions further comprising one or more other components.

In some embodiments, the compositions and methods disclosed herein can be used to deliver an agent to a subject.

The present invention enables the delivery of drugs or other diagnostic or imaging agents that are associated with the MBC. In some embodiments, the MBC is utilized as a delivery vehicle for drug encapsulated particles.

The drug can be a therapeutic, diagnostic, and/or imaging agent.

An agent suitable for delivery by the MBC of the invention may be a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that are man-made in that they are designed, engineered, and/or produced through action of the hand of man and/or are not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, siRNAs, shRNAs, DNA/RNA hybrids, antisense oligonucleotides, ribozymes, peptides, peptide mimetics, peptide nucleic acids, small molecules, etc. In some embodiments, an agent is or comprises a polymer. In some embodiments, an agent contains at least one polymeric moiety.

The term "imaging agent" as used herein refers to any element, molecule, functional group, compound, fragments thereof or moiety that facilitates detection of an agent to which it is joined.

A therapeutic agent suitable for delivery by the MBC of the invention may be any agent that has a therapeutic effect and/or elicits a desired biological and/or pharmacological effect, when administered to a subject.

One embodiment of the invention relates to the MBC further comprising albumin.

Human serum albumin (HSA) is the most abundant serum protein, and plays a role in numerous biological and physiological activities. It is retained in the plasma due to its relatively high molecular weight and the stability of its tertiary structure. HSA contains 585 amino acid residues, a large percentage of which are ionic, making the protein highly soluble.

HSA also acts as a carrier for endogenous and exogenous biomolecules such as peptides, proteins, hormones or drugs. HAS improves one or more properties of a biomolecule to which it is linked. The one or more properties may be selected from the group consisting of improved pharmacokinetics, increased shelf-life, increased solubility, increased affinity for the target and increased biological activity.

HAS polymers are used for tissue engineering and tissue repair applications (See for example Li P S et al). Commercially available albumins from animals are generally provided in dried and lyophilized powders. These powders are dissolved in a suitable reaction buffer to make an albumin solution. In order to be able to utilize HSA for tissue engineering and tissue repair applications, liquid albumin solution must first be converted into an albumin polymer and then be converted into a solid-state scaffold by various fabrication methods known in the art.

In a chemically cross linking reaction, a soluble albumin may polymerize and become insoluble. Such cross linking reactions change the molecular structure of albumin and reduce its ability to participate in biological and physiological activities. In addition, cross-linkers are frequently toxic. Thus utilizing HSA for regenerative medicine is a cumbersome multi-stage and potentially toxic process.

In contrast, in accordance with one embodiment of invention serum albumin is incorporated into the MBC, thus the MBC combines the beneficial properties of HSA with its various other properties.

One embodiment of the invention relates to the composition further comprising growth factors. The growth factors may be included in a solution together with any other component or may be supplied in a separate solution. Such growth factor may aid in creating the best possible condition for the effector cells delivered to or already present at the wound site. Application of growth factors together with the fibrin sealant saves a step in the wound treatment procedure.

In one embodiment of the invention the growth factors are selected from the group consisting of Epithelial Growth Factor (EGF), Fibroblast Growth Factor (FGF), Platelet Derived Growth Factor (PDGF), Transforming Growth Factor alpha (TGFα), Transforming Growth Factor beta (TGFβ) and Interleukin-1.

The modified blood clot (MBC) compositions disclosed hereinabove are useful in promoting or enhancing therapeutic processes, including, without limitation, hemostasis and healing, wound healing, graft or medical device fixation, sealing of anastomosis sites, soft tissue reconstruction/repair, soft tissue filling, dermal filling, skin fixation, dural repair, burn treatment, bleeding control, tissue regeneration and drug and cell therapy. For example, the MBC can adhere to wounds and tissue surfaces and be used to control bleeding, promote healing (e.g. wound healing) and reconstruct tissues and organs.

As used herein the terms "promoting" or "enhancing" a therapeutic process refer to support, magnification, intensification of a therapeutic process which results in partial or complete alleviation, amelioration, relief, inhibition, reduction in severity of, and/or reduction in the incidence of one or more symptoms, features, and/or causes of a particular disease, disorder, and/or condition.

The term "tissue" as used herein refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue, tissue-engineered analogues thereof.

The term "tissue regeneration" as used herein, refers to the restoration, full or in part, of a structure or a function of a tissue that exhibits a loss or impairment of that structure or function, for example, as a consequence of a disease or injury. The restoration of blood flow to an ischemic, hypoxic, or anoxic tissue, the restoration of the mechanical function of a broken bone, the restoration of neural function to a brain or spinal cord region after traumatic injury, or the restoration of glucose-responsive insulin production to pancreatic tissue of a type I diabetic are non-limiting examples of tissue regeneration. Additional examples will be apparent to those of skill in the art and the disclosure is not limited in this respect.

As used herein the term "organ" refers to a solid vascularized organ that performs a specific function or group of functions within an organism. The term organ includes, but is not limited to, heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus.

As used herein, the term "promotes wound healing" means that administration of the MBC or a pharmaceutical composition comprising the MBC decreases the time required for 90% wound closure by at least 1 day relative to a control wound not treated with the MBC or the composition. Preferably, a treatment that promotes healing will decrease the time necessary to heal a wound by 2 days or more, 3 days or more, 4 days or more, 5 days or more, 6 days or more, or even 7 days (one week) or more.

As used herein, a "surface" is a position or location where one desires to apply the modified blood clot. The surface depends on the use of the modified blood clot. The modified blood clot may be used, for example, for sealing a surgical wound, in vascular surgery including providing hemostasis, tissue graft fixation, organ graft fixation, wound healing and anastomosis, such as arterial, gastrointestinal and tracheal anastomoses.

The surface can be an external bodily surface, e.g. skin that can be seen by unaided vision or a surface of an internal body part which is a part of the internal anatomy of a subject. External surfaces include, but are not limited to, the skin of the face, throat, scalp, chest, back, ears, neck, hand, elbow, hip, knee, and other skin sites. Examples of internal body parts include, but are not limited to, body cavity or anatomical openings that are exposed to the external environment and internal organs such as the nostrils; the lips; the ears; the genital area, including the uterus, vagina and ovaries; the lungs; the anus; the spleen; the liver; a blood vessel and the cardiac muscle. The surface can be a bleeding or a non-bleeding site in a subject.

A "subject" as used herein, refers to the patient to which the MBC is administered. The term includes animals, e.g. mammals, including humans. In one embodiment, a subject is a surgery patient or a wounded patient.

Wounds amenable to treatment with the MBC of the invention are typically in the form of burns, punctures, cuts or tears of the living tissues. Wounds of the skin can penetrate the epidermis, dermis or in the case of full-thickness wounds, the subcutaneous tissue. Thus, representative types of wounds amenable to treatment with the MBC compositions of the present invention include burns (e.g., caused by exposure to fire or an agent that is highly caustic to skin), ulcers (e.g., pressure ulcers, venous ulcers, and diabetic ulcers), tendonitis; surgical wounds associated with coronary operations; and post-operative wounds following abdominal and any other types of surgery. Other wounds are those which result from trauma such as incurred during combat or other violent activity, including wounds caused by gun shots, knives, or any other object able to cause a cut or tear in the skin. Wounds of the oral cavity (e.g., teeth), as well as wounds that arise as a side-effect of medication or as a symptom of various pathologies (e.g., sores associated with Kaposi's Sarcoma), as well as internal wounds (e.g. ruptures of muscle tissue such as anal fissures), and wounds or lesions to the gastrointestinal tract, such as ulcers in the stomach or intestines) may also be amenable to treatment with the MBC of the present invention.

The MBC composition of the present invention may also be used to treat any wounds or injuries exacerbated by vascular insufficiency. Vascular insufficiency, for purposes of the present invention, refers to inadequate blood circulation resulting in insufficient perfusion to the afflicted areas. Such insufficiency can be caused by trauma (e.g. damage to the vasculature adjacent to a skeletal fracture), or various pathologies (e.g. diabetes and atherosclerosis). In either instance, whether trauma or disease induced, vascular insufficiency decreases the likelihood of effective wound healing. The MBC composition may be useful in improving wound healing outcomes in these patients.

In one embodiment the MBC composition is useful in treating diabetic foot ulcers or chronic pressure ulcers of the skin and underlying tissues caused by prolonged pressure and impeded blood flow on the body surface of bedridden patients. At least 48% of stage IV pressure ulcers remain unhealed after one year of treatment.

In other aspects, the invention is directed to a method of inhibiting the onset of infection in a wound, comprising administering to the wound the MBC composition of the invention. In one embodiment, the wound is caused by trauma. In another embodiment, the wound is caused by surgery.

In those aspects involving methods of treating a wound, the wound may also be treated by administering to the wound an article of manufacture comprising the MBC composition of the invention.

In one embodiment, application of the MBC composition is accomplished by means of one or more injections of the MBC composition directly into the wound or the tissue surrounding the wound. The MBC composition may be applied directly into an open wound.

The MBC composition may be injected into the wound in various locations. In one embodiment, injection occurs about every one centimeter to about every three centimeters for the entire length of the wound. In other embodiments, the MBC composition is administered at a single site within the wound. The biological space of a wound, particularly a pressure wound, is often limited. When injecting into a wound, there is a risk of pressure causing the syringe to separate from the needle. Using a locking syringe eliminates this risk. If the 18 G or larger needle is used for aspiration, it is exchanged with a needle ranging in size from 22-35 G for injection into a wound.

When injection into the wound tissue is not possible, the MBC composition can be applied directly into the cavity of the wound. Application in this method can be performed using direct application with a syringe or tubing.

The MBC composition may be applied to or around the wound site with the aid of a dressing. Dry dressings include gauze and bandages, non-adhesive meshes, membranes and foils, foams, and tissue adhesives. Moisture-keeping barrier dressings include pastes, creams and ointments, non-permeable or semi-permeable membranes or foils, hydrocolloids, hydrogels, and combination products. Bioactive dressings include antimicrobial dressings, interactive dressings, single-component biologic dressings, and combination products (e.g., ointments, gels, fibrin sealant, growth and angiogenic factors (e.g., PDGF, VEGF or collagen). In some embodiments, the wound is packed with sterile gauze soaked in the MBC composition. The dressing, e.g., such as sterile gauze pads, may be saturated with other compositions such as Lactated Ringer's (Hartmann's) solution, alginate-containing dressing, or polyurethane dressing, which is applied to cover the wound, followed by application of dry dressing. If the subject wound is highly infected, then silver dressings can be applied. The choice of post-injection dressing is based on the determination of the clinician. Commercial availability, history of past clinical success, and patient tolerance are all factors to be considered in the selection of a wound dressing. The dressing may be removed periodically, e.g., typically after about 24 hours, in order to irrigate the wound e.g., with sterile water and soap.

The composition may be applied to the wound once or more than once, e.g., after 4 weeks, once a clinician determines whether another application is necessary. Factors that may be taken into account include increased wound dimensions (width, length and depth), suppuration, pyrexia or any other sign or symptom indicating a recalcitrant wound infection such that re-treatment is warranted. In addition to re-treatment, referral for surgical debridement may be indicated at any point the clinician deems appropriate.

The composition may be used in conjunction with any other conventional wound treatment, such as warming (therapeutic heat), electrical stimulation, magnetism, laser phototherapy and ultrasound. It also can be used with biological therapy such as skin substitutes, cultured keratinocytes (Epicel, Genzyme biosurgery), human dermal replacement (Dermagraft, Smith and Nephew Inc.), cadaver derived processed dermis (Alloderm, Life Cell Corporation), Bilayered Skin Equivalent (Apligraf, Organogenesis Inc.), TransCyte (Smith and Nephew Inc.), Growth Factors (e.g. PDGF), and fibrin sealant. In some embodiments, the MBC composition is used in conjunction with VAC, which is a commercially available wound therapy manufactured by KCI. VAC promotes wound healing by applying negative pressure to a wound. In these embodiments, the composition is preferably applied to a wound prior to VAC therapy. The composition can be applied to a wound just prior to a patient receiving hyperbaric therapy. The composition may also be used in conjunction with low-energy shock wave therapy (e.g., impulses of about 0.1 mJ/ram2; 5 Hz) per centimeter of wound length. (See e.g., Dumfarth, et al, Ann. Thorac. Surg. 55: 1909-13 (2008). After treatment, the wounds may be evaluated for length, width and height measurements. Typically, a wound is considered healed when all measurements of these parameters are negligible.

The MBC composition of the invention can be administered in a range of frequencies that will vary with the type of wound or tissue being treated and the exact formulation of the composition, choice of a suitable dosage form is well within the capabilities of the physician.

The MBC composition can be administered, for example, once when an internal wound surface is to be treated, prior to suturing or otherwise closing the external access to the internal wound surface. For other wounds, e.g., those on an external surface or on an internal surface accessible with non-surgical approaches, application can be more frequent, e.g., an initial application, followed by re-application within hours, e.g., 4 hours, 8 hours, 12 hours, etc., or, more likely, followed by re-application once or twice daily, for example, until the wound is healed. In practicality, any range of re-application that maintains the rate of healing can be used by the ordinarily skilled practitioner.

Efficacy of treatment can be judged by an ordinarily skilled practitioner. Clearly, where a chronic wound is involved, any healing that leads to closure or healing of the wound involves effective treatment. Alternatively, where the wound is not a chronic wound, e.g., an acute surgical wound, changes in the time required to close the wound (i.e., in the rate of healing) will be apparent to the ordinarily experienced practitioner based on their frequent experience with similar wounds.

A further aspect of the invention provides a pharmaceutical composition comprising the modified blood clot of the invention in admixture with a pharmaceutically acceptable adjuvant, diluent or carrier.

As used herein the terms "pharmaceutical composition" or "pharmaceutical formulation" mean any composition intended for administration to a human being or other mammal and comprises as at least one active agent the modified blood clot of the invention; it may also include one or more other additives, for example pharmaceutically acceptable excipients, carriers, penetration enhancers, stabilizers, buffers or other materials.

The term a "pharmaceutically acceptable adjuvant, diluent or carrier" refers to reagents, compounds, materials, compositions, diluents that are compatible with the constituents in the formulation and suitable for use in contact with the tissues of human beings and animals without excessive toxicity, irritation, allergic response, or other complication commensurate with a reasonable benefit/risk ratio. A pharmaceutically acceptable carrier which is suitable for use with the modified blood clot disclosed herein may be, but is not limited to, liquids, semi-solid and solid materials.

The optimal pharmaceutical composition will be determined by one skilled in the art depending upon, for example, the intended route of administration, delivery format and desired dosage.

In one embodiment, the pharmaceutical composition may be in a form selected from the group consisting of a balm, solution, suspension, emulsion, ointment, foam, paste, gel, cream, lotion, powder, salve, soap, surfactant-containing cleansing, oil, serum, drops, liposomes, nanoparticles, and spray. In other embodiments, the composition may be a cream, lotion, or solution. In other embodiments, the composition may be impregnated or made part of a bandage. In other embodiments, the bandage may be a surgical dressing, a plaster bandage, an adhesive bandage, or gauze.

Once the pharmaceutical composition has been formulated, it may be stored in sterile containers as a solution, suspension, gel, emulsion, solid, or as a dehydrated or lyophilized powder. Such formulations may be stored frozen. Such formulations may be stored either in a ready-to-use form or in a form (e.g., lyophilized) that is reconstituted prior to administration.

The composition of this invention can be admixed, encapsulated, conjugated or otherwise associated with other molecules, molecule structures or mixtures of compounds, for example, liposomes, receptor targeted molecules, oral, rectal, topical or other formulations, for assisting in uptake, distribution and/or absorption in a recipient, using methods that are well known in the pharmaceutical arts.

In one embodiment, the pharmaceutical composition may further comprise a component selected from the group consisting of monocytes, stem cells, gene therapy products, vitamins, palmitate retinol, tocoferil acetate, sodium ascorbil phosphate, D-panthenol, peptides, recombinant growth factors, micronized human-identical hormones, aminoacids, phyto-extracts, antioxidants, lipoic acid, DMAE, collagen, GAG, hyaluronic acid, proteoglycans, adenine, guanine, cytosine, thymine, trace elements, minerals, proteases, ceramides, polisaccarides, algae, and marine extracts.

The composition of the invention can further comprise biodegradable or nonbiodegradable reinforcing elements, also termed herein enhancing agents. The enhancing agents may be added at the liquid or pliable form stage of the preparation of the composition (i.e. prior to the assembly of the insoluble network of the composition), or applied onto the composition after it is formulated.

The composition of the invention may be administered to an individual in need thereof in a wide variety of ways. Preferred modes of administration include topical, oral, rectal, by inhalation or spray, intravenous, intravascular, intramuscular, subcutaneous, intracerebral, intraperitoneal, soft tissue injection, surgical placement, endoscopic placement, localized administration and percutaneous insertion, e.g. direct injection, cannulation or catheterization. Any administration may be a single application of the composition of the invention or multiple applications. Administrations may be to single site or to more than one site in the recipient. Multiple administrations may occur essentially at the same time or separated in time.

As used herein, the term "administering", "administered" or "administration" includes any method of delivery of a pharmaceutical composition or therapeutic agent into a subject's system or to a particular region in or on a subject.

The invention also provides a method of treating an injury, trauma, or the loss of blood in a subject, comprising applying a therapeutically effective amount of the MBC composition of the current invention to the site of injury, trauma or blood loss.

A "therapeutically effective amount" means an amount of the MBC or a composition comprising the MBC that facilitates the desired therapeutic effect e.g. sealing, healing and/or reducing blood loss in the subject, or treating, preventing, alleviating or reducing at least one symptom of a medical condition in a subject.

As used herein, the term "treatment" (and also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The MBC composition may be suspended in a medium or included in a tissue or in a natural or synthetic tissue repair matrix, such as but not limited to bioresorbable collagen scaffold or matrix or incorporated into a bandage or wound closure devices.

In another embodiment, the invention provides a method of treating an ischemic tissue, such as myocardial tissue, skeletal muscle tissue, bone tissue, cartilage tissue, neuronal tissue, hepatic tissue, renal tissue and skin tissue.

In one embodiment, one or more agents are added to the modified blood clot or the pharmaceutical composition of the invention. Non-limiting examples of such agents include calcium, aprotinin, fibrinogen, collagen, thrombin, hyaluronic acid, factor XII, fibronectin, plasminogen, antifribinolytic agents (e.g. transexamic acid), stabilizers (e.g. arginine hydrocholoride), platelet activators, WBC activating factors, vitamin K-dependent clotting zymogens.

In an alternate embodiment, the composition is substantially free of added protease inhibitors.

In another aspect, provided is a container holding the composition of the invention. The container may be for example, an ampoule, a vial or syringe. The containers can be made of for example, glass, metal or plastic.

In another aspect, provided is a kit comprising a container such as an ampoule, a vial, a test tube or a syringe which includes the composition of the invention as disclosed hereinabove; optionally the kit includes a thrombin component and/or instructions for use.

Biological materials derived from blood components are typically purified from infective particles in order to minimize the potential risk posed by blood-borne pathogens. The purification procedure can be carried out by nanofiltration, solvent/detergent (S/D) treatment, heat treatment, gamma or UVC (<280 nm) irradiation, or by any other method known in the art.

The term "infective particle" refers to a microscopic particle, such as, but not limited to, a microorganism or a prion, which can infect or propagate in a biological organism. The infective particles can be viral particles. The inactivation procedure of infective particles can be carried out by adding an inactivating molecule to a solution prior to and/or during the procedure. The added molecules and their products can be removed by gravitation, column chromatography phase separation or by any other method known in the art. The removal of infective particles can be carried out by filtration or by selective absorption methods such as affinity, ion exchange or hydrophobic chromatography.

A multi-step viral inactivation procedure can be carried out, for example, by combining two or more of the following: solvent/detergent treatment, pasteurization, selective chromatography and nanofiltration.

The term "viral inactivation" refers both to the situation wherein viruses are maintained in a solution but are rendered non-viable (for example, by dissolving their lipid coat), and/or to the situation wherein viruses are physically removed from the solution (for example, by size exclusion techniques).

The MBC formulation is preferably sterile and free from pathogens, for example by pasteurization and/or filtration.

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%.

EXAMPLES

While the following examples demonstrate certain embodiments of the invention, they are not to be interpreted as limiting the scope of the invention, but rather as contributing to a complete description of the invention.

Preparation of MBC

I. Spontaneously-forming blood clots were prepared as follows: human umbilical cord whole blood was collected into glass tubes without anticoagulant and allowed to clot at room temperature for 1 hour.

II. Recalcified blood clots were prepared as follows: human umbilical cord whole blood samples were collected into polypropylene blood collection tubes (BD Vacutainer) containing 3.2% sodium citrate. Samples were recalcified with 10 mM CaCl2 (final concentration) and allowed to clot at room temperature for 1 hour.

III. Thrombin-induced blood clots were prepared as follows: human umbilical cord whole blood samples were collected into polypropylene blood collection tubes (BD Vacutainer) containing 3.2% sodium citrate. Samples were recalcified with 10 mM CaCl2 (Sigma) (final concentration) and mixed with 2 NIH (National Institute of Health) Units/ml bovine thrombin (Sigma) to induce fibrin formation. Then the samples were allowed to clot at room temperature for 1 hour.

Figure 1B:
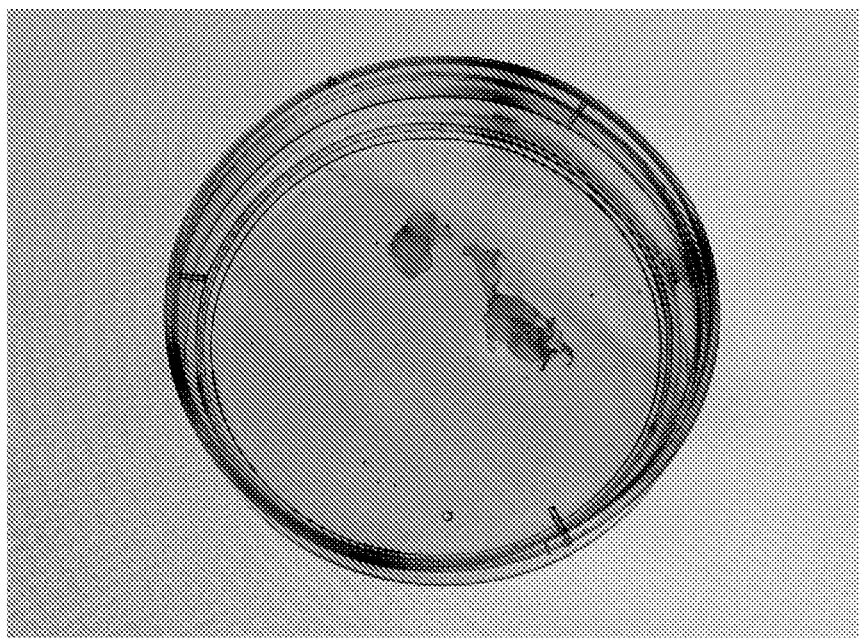

Blood clots formed by any of the above methods were further modified as follows:

The blood clots were washed with PBS in order to remove access of blood, then exposed to a modifying compound, for example 0.1% sodium dodecyl sulfate or RBC lysis buffer containing protease inhibitor cocktail (1:1000) at 4° C. under constant agitation, for a duration of up to 6 days, until the clots become whitish and semitransparent (FIG. 1). Then the samples are washed with deionized (DI) water followed by PBS at 4° C. under constant agitation and kept in 4° C. for further analysis.

Figure 2:
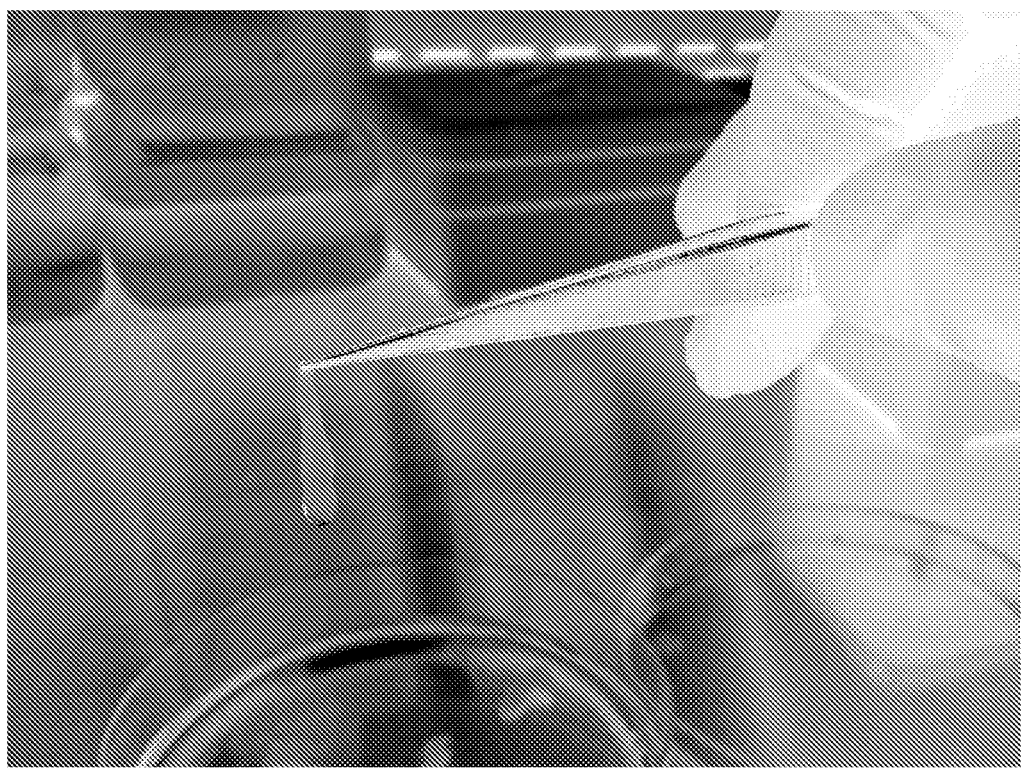
FIG. 2 is a macroscopic view of a spontaneously forming blood clot demonstrating its capacity to bind water.

The spontaneously formed blood clots were capable of binding water. Water plays a major role in any biological reaction and is an active participant determining the physical properties of biomaterials. Thus, wettability (ability to absorb water) is one of the most important parameters affecting the biological response to a biomaterial upon implantation. In order to qualitatively demonstrate bound water content or water holding capacity, an MBC generated from spontaneously formed blood clot was immersed in DI water for 10 minutes. Then, access of water was gently removed using a filter paper, and the MBC was held using forceps, demonstrating its capacity to hold water (FIG. 2).

Figure 3A:
FIG. 3A-3G are macroscopic views demonstrating various 3D shapes of MBC.
Figure 3B:
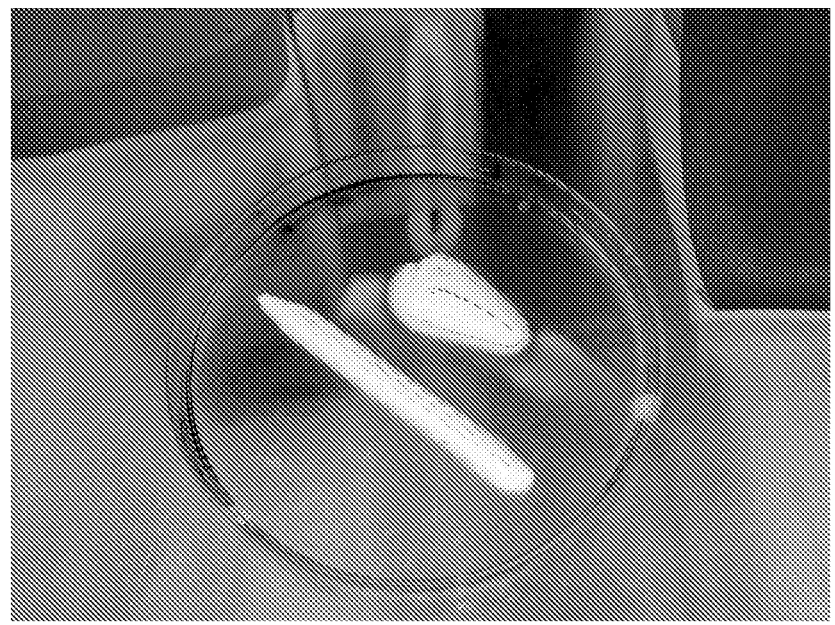
Figure 3C:
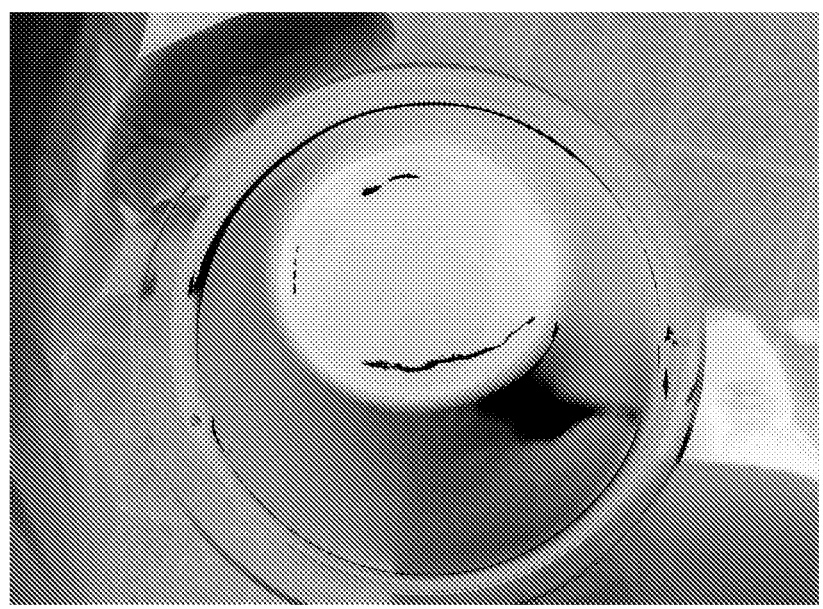
Figure 3D:
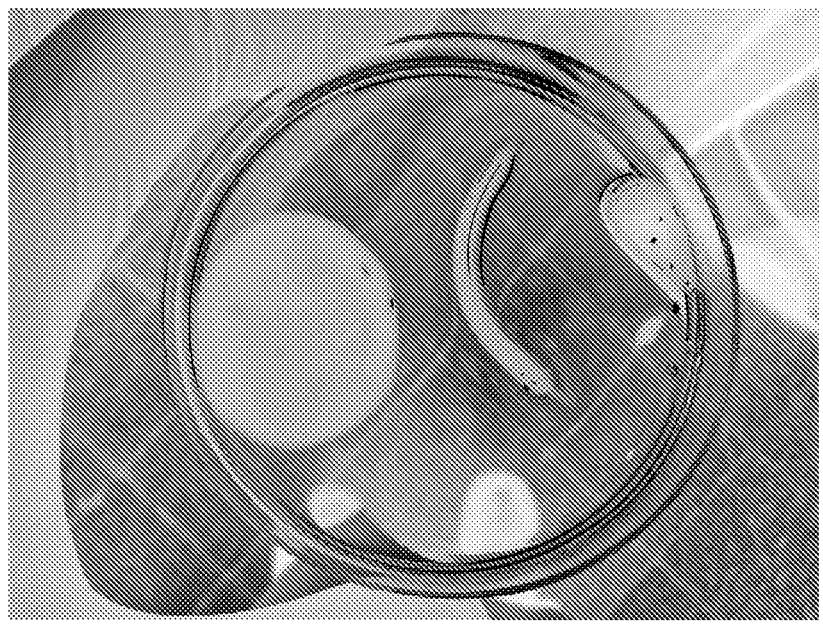
Figure 3E:
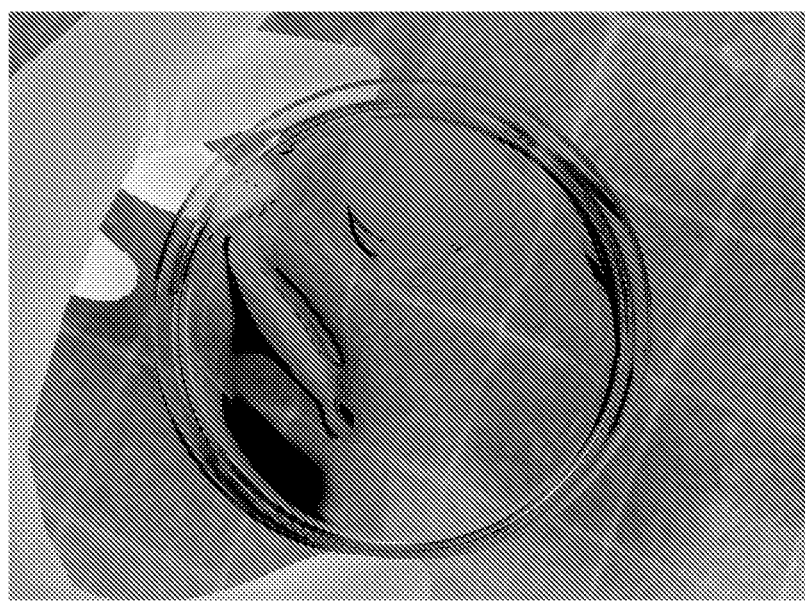
Figure 3F:
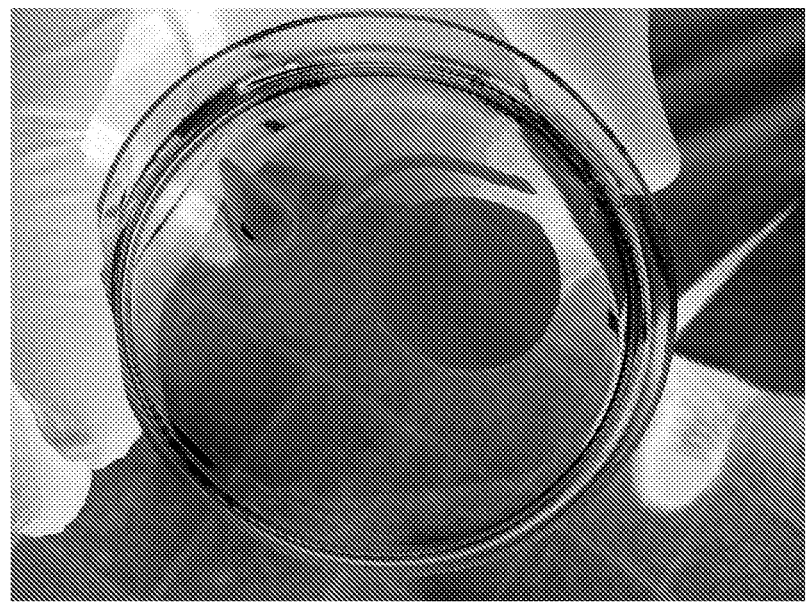
Figure 3G:
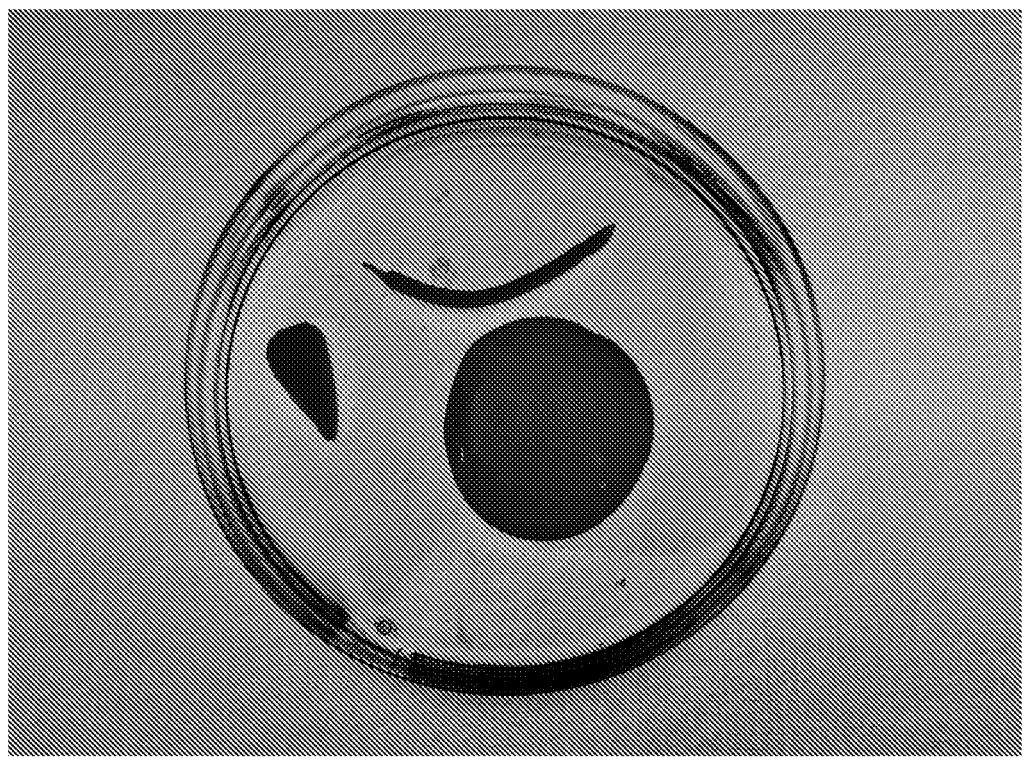

The blood clots can be formed in differently shaped containers thus resulting in various three dimensional shapes, suited for the therapeutic need. For example, the clot can be formed in a syringe, or a petri dish or a tube and thereby assume a desired shape. Thrombin-induced MBC was generated as described above. Briefly, citrated human umbilical cord whole blood was transferred into three containers: a 15 ml polypropylene centrifuge tube, a 60 mm petri dish and 1 ml syringe (FIG. 3A). Next, the blood in each container was recalcified with CaCl2 and mixed with bovine thrombin, and was allowed to clot at room temperature for 1 hour. FIGS. 3B-3C show generated blood clots prior to modification, assuming the shape of the corresponding container. Next, the generated blood clots were washed with PBS and exposed to 0.1% sodium dodecyl sulfate solution containing protease inhibitor cocktail (1:1000) at 4° C. under constant agitation. The progressive modification of the generated blood clots after 2 days, 3 days and 5 days is shown in FIGS. 3D, 3E and 3F, respectively. At 5 days, the generated MBC became whitish and semitransparent (FIGS. 3F and 3G).

Figure 4A:
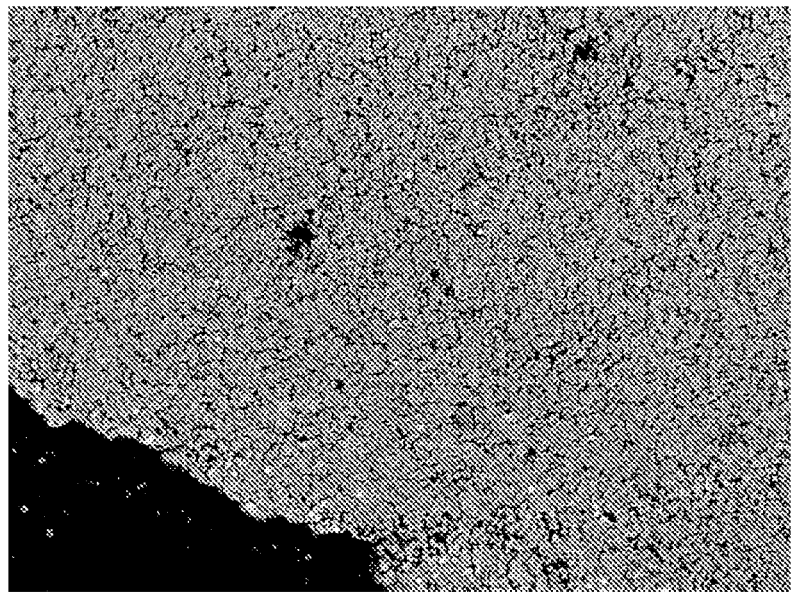
FIG. 4 is a photomicrograph of hematoxylin-eosin (H&E)-stained histological sections of an unmodified blood clot at ×200 (FIG. 4A) and ×400 (FIG. 4B) magnification.
Figure 4B:
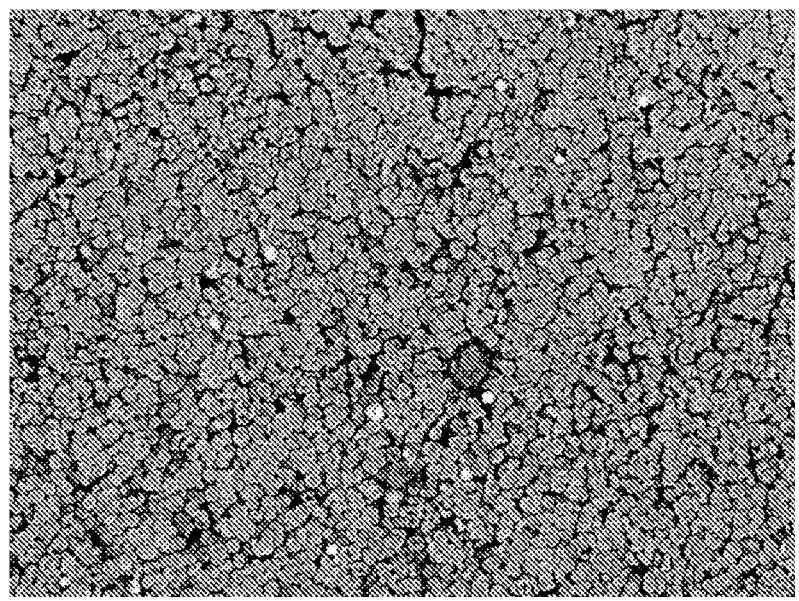
Figure 5A:
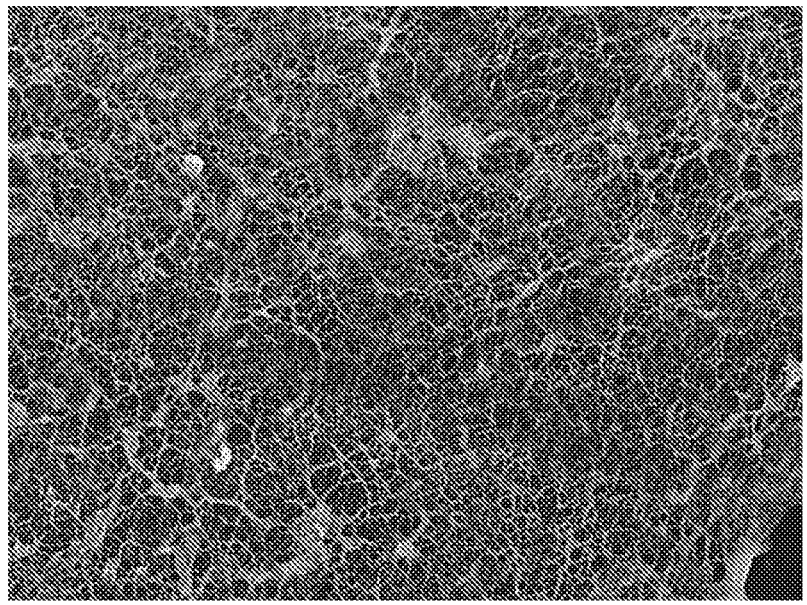
FIGS. 5A and 5B are photomicrographs of H&E-stained histological sections of MBC at ×400 magnification.
Figure 5B:
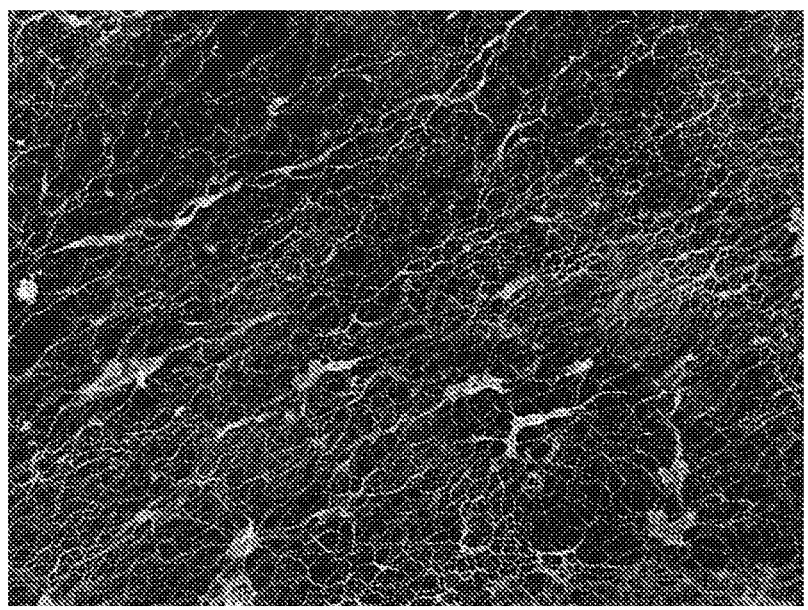
Figure 6A:
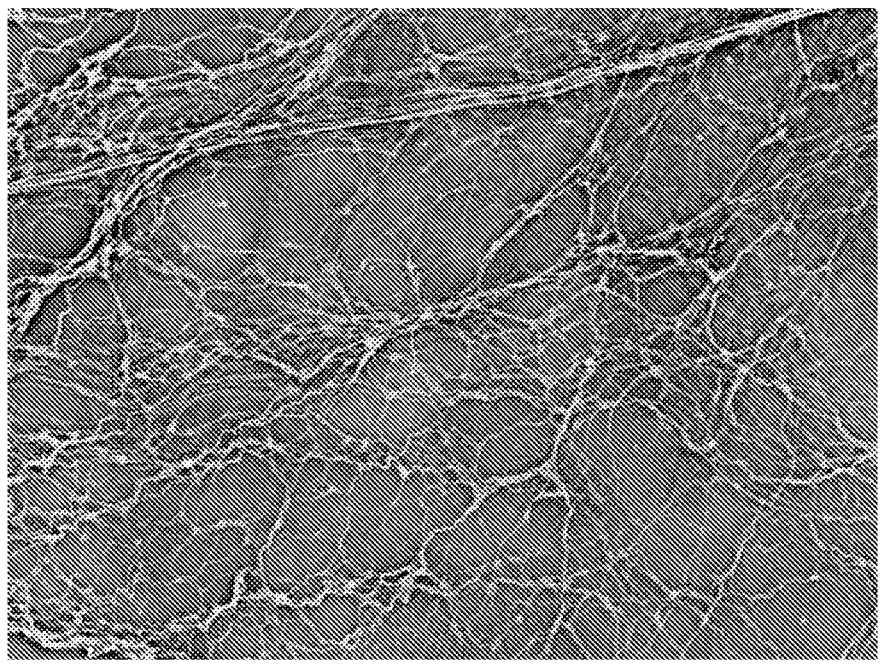
FIGS. 6A, 6B and 6C are inverted microscope images of MBC at ×200 magnification.
Figure 6B:
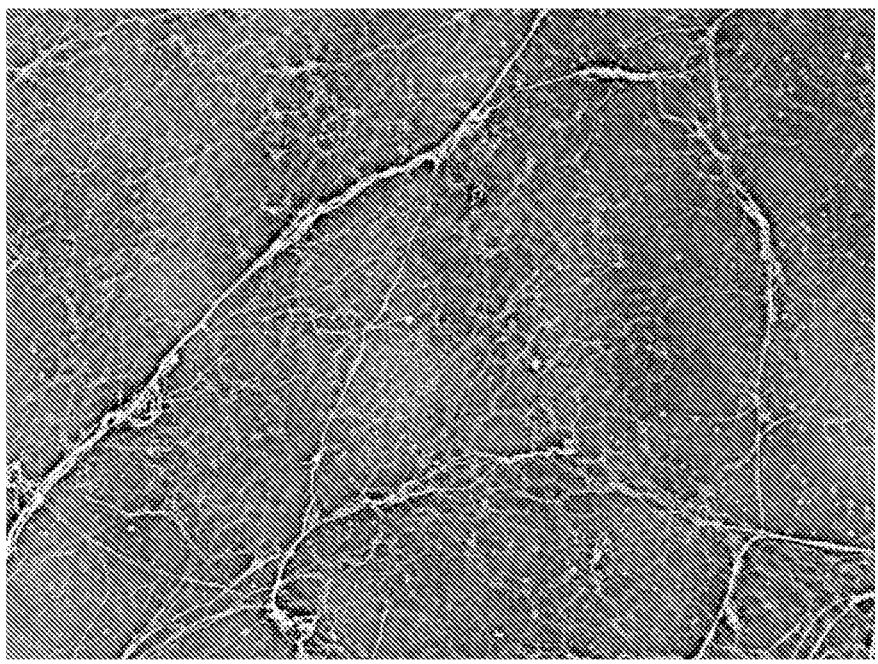
Figure 6C:
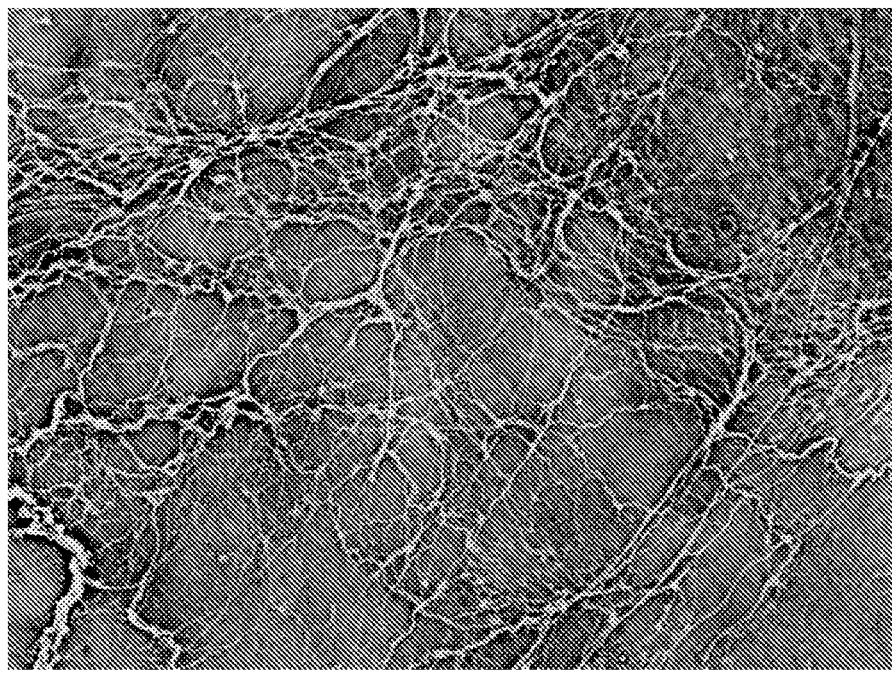

The microscopic structure of the modified blood clots was analyzed using hematoxylin & eosin (H&E) histological staining of tissue sections. Fresh, unmodified blood clots or MBC were fixed for at least 24 hours in 4% formalin and then embedded in paraffin, serially sectioned, mounted on glass slides and stained with Hematoxylin and Eosin (H&E) for light microscopy. The histological appearance of an unmodified, normal blood clot is shown in FIG. 4, showing typical RBC aggregate and occasional WBC embedded in fibrin mesh. The structure of a modified clot is shown in FIG. 5, showing the absence of cellular material, revealing highly porous, well-preserved fibrin matrix architecture. The morphological features of the modified blood clots were further viewed using an inverted microscope (FIG. 6). The blood clot shown in FIG. 6 was incubated with the modification agent for 10 minutes.

Figure 7A:
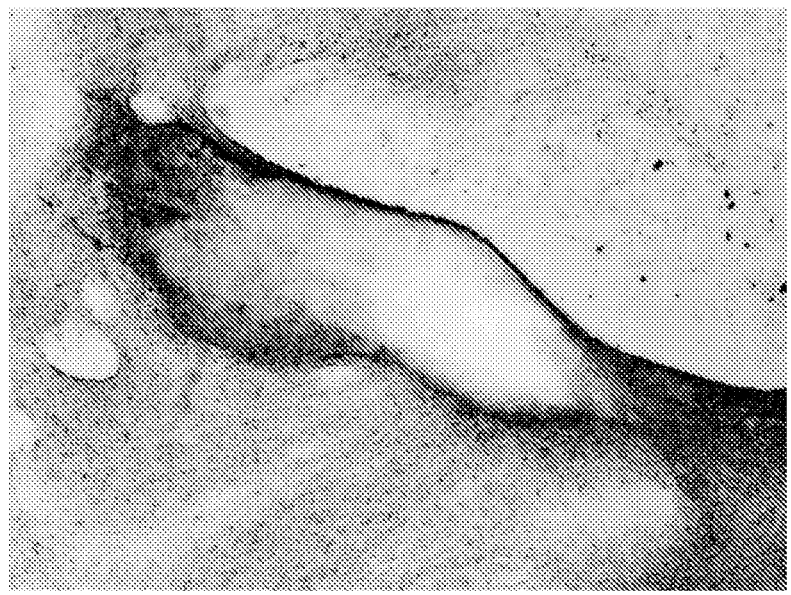
FIGS. 7A and 7B are inverted microscope images of MBC in culture fully covered with placenta-derived cells at ×40 and ×200 magnification, respectively.
Figure 7B:
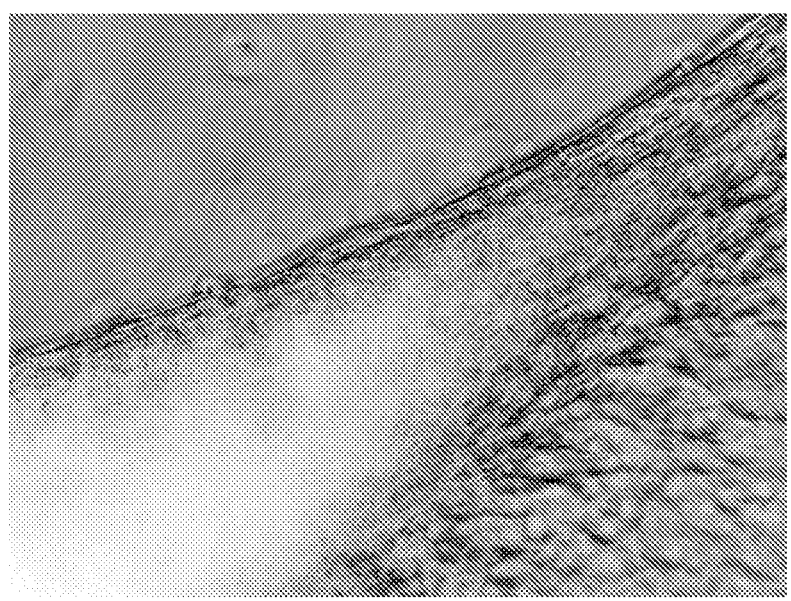
Figure 7C:
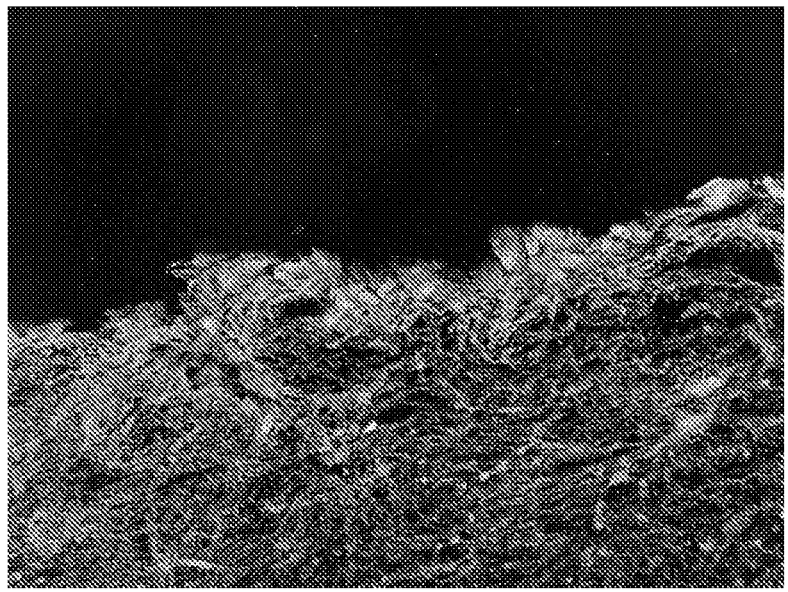
FIGS. 7C and 7D are H&E-stained histological sections of MBC seeded with placental cells at ×200 magnification.
Figure 7D:
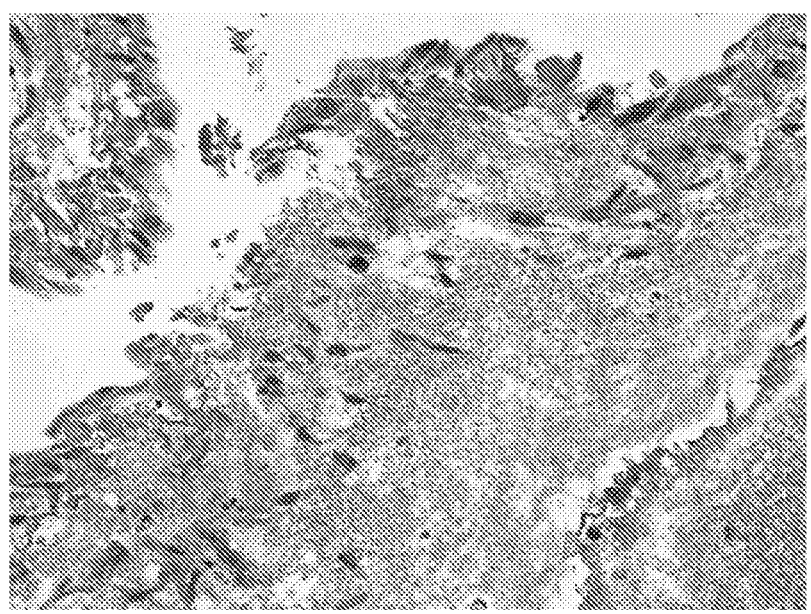

Next, the modified blood clot was seeded with placenta-derived cells. Briefly, placental tissue was aseptically obtained with informed consent from healthy woman after a caesarian section. Placental cells were isolated and seeded on tissue culture plates and cultured in the presence of DMEM supplemented with 10% FBS and 1% antibiotics. Next, the cells were detached from the culture plates using trypsin, seeded on MBC and maintained in culture for additional 10 days. As shown by inverted microscope images in FIGS. 7A and 7B, the seeded placental cells readily populated the MBC and fully covered it. H&E-stained histological sections of MBC seeded with placental cells shown in FIGS. 7C and 7D confirmed high level of cell adherence, proliferation both on the surface of the MBC and at deeper layers towards the center of the MBC.

Mass Spectrometry (MS) Analysis

A modified blood clot generated as described above was digested by trypsin and analyzed by LC-MS/MS on Q-Exactive Mass spectrometer (Thermo). The MS files were viewed using QualBrowser (ThermoFisher Scientific). Peak lists obtained from MS/MS spectra were identified using Byonic (Protein Metrics Inc).

Protein identification was conducted against a concatenated target/decoy [PMID 20013364] version of the *Homo sapiens* complement of the UniProtKB [PMID 14681372] (49,888 sequences). The decoy sequences were created by reversing the target sequences in Byonic. The identification settings were as follows: Trypsin with a maximum of 2 missed cleavages; 10.0 ppm (parts per million) as MS1 and 20.0 ppm as MS2 tolerances; fixed modifications: Carbamidomethylation of C (+57.021464 Da). Variable modifications: Deamidation of N and Q (+0.984016 Da), Oxidation of M and P (+15.994915 Da), Phosphorylation of S, T and Y (+79.966331 Da), Acetylation of protein N-term (+42.010565 Da), Hex (+162.0528) and HexNAc (+203.0794) of S, T and N. Maximum of 3 modifications were allowed.

Peptide Spectrum Matches (PSMs), peptides and proteins were validated at a 0.8% False Discovery Rate (FDR) estimated using the decoy hit distribution. Results were inspected manually, and filtered for minimum 2 peptides per proteins and >200 confidence score, resulting in 324 high confidence unique proteins.

Results:

A total of 324 proteins (see Table 1: Protein List) were identified in MBC derived from human umbilical cord blood.

TABLE 1 protein list:

>sp|P02671|FIBA_HUMAN Fibrinogen alpha chain OS = *Homo sapiens* GN = FGA PE = 1 SV = 2
>sp|P02675|FIBB_HUMAN Fibrinogen beta chain OS = *Homo sapiens* GN = FGB PE = 1 SV = 2
>sp|P02679|FIBG_HUMAN Fibrinogen gamma chain OS = *Homo sapiens* GN = FGG PE = 1 SV = 3
>sp|P02751|FINC_HUMAN Fibronectin OS = *Homo sapiens* GN = FN1 PE = 1 SV = 4
>sp|HBA_HUMAN|(Common contaminant protein)
>sp|P01857|IGHG1_HUMAN Ig gamma-1 chain C region OS = *Homo sapiens* GN = IGHG1 PE = 1
SV = 1
>sp|P69892|HBG2_HUMAN Hemoglobin subunit gamma-2 OS = *Homo sapiens* GN = HBG2 PE = 1
SV = 2
>sp|P11678|PERE_HUMAN Eosinophil peroxidase OS = *Homo sapiens* GN = EPX PE = 1 SV = 2
>tr|A0A087WWV8|A0A087WWV8_HUMAN Protein IGKV1-8 OS = *Homo sapiens*
GN = IGKV1-8 PE = 4 SV = 1
>sp|P0C0L4|CO4A_HUMAN Complement C4-A OS = *Homo sapiens* GN = C4A PE = 1 SV = 2
>sp|P06702|S10A9_HUMAN Protein S100-A9 OS = *Homo sapiens* GN = S100A9 PE = 1 SV = 1
>sp|P21980|TGM2_HUMAN Protein-glutamine gamma-glutamyltransferase 2
OS = *Homo sapiens* GN = TGM2 PE = 1 SV = 2
>sp|Q5SSJ5|HP1B3_HUMAN Heterochromatin protein 1-binding protein 3 OS = *Homo sapiens*
GN = HP1BP3 PE = 1 SV = 1
>sp|P05109|S10A8_HUMAN Protein S100-A8 OS = *Homo sapiens* GN = S100A8 PE = 1 SV = 1
>sp|Q6P995|F171B_HUMAN Protein FAM171B OS = *Homo sapiens* GN = FAM171B PE = 2 SV = 3
>sp|P01023|A2MG_HUMAN Alpha-2-macroglobulin OS = *Homo sapiens* GN = A2M PE = 1 SV = 3
>sp|P35527|K1C9_HUMAN Keratin, type I cytoskeletal 9 OS = *Homo sapiens* GN = KRT9 PE = 1
SV = 3
>sp|P27105|STOM_HUMAN Erythrocyte band 7 integral membrane protein OS = *Homo sapiens*
GN = STOM PE = 1 SV = 3
>sp|P06396|GELS_HUMAN Gelsolin OS = *Homo sapiens* GN = GSN PE = 1 SV = 1
>sp|P08697|A2AP_HUMAN Alpha-2-antiplasmin OS = *Homo sapiens* GN = SERPINF2 PE = 1
SV = 3
>sp|P02730|B3AT_HUMAN Band 3 anion transport protein OS = *Homo sapiens* GN = SLC4A1
PE = 1 SV = 3
>sp|P05164|PERM_HUMAN Myeloperoxidase OS = *Homo sapiens* GN = MPO PE = 1 SV = 1
>sp|P60709|ACTB_HUMAN Actin, cytoplasmic 1 OS = *Homo sapiens* GN = ACTB PE = 1 SV = 1
>sp|Q13201|MMRN1_HUMAN Multimerin-1 OS = *Homo sapiens* GN = MMRN1 PE = 1 SV = 3
>sp|P01024|CO3_HUMAN Complement C3 OS = *Homo sapiens* GN = C3 PE = 1 SV = 2
>sp|P00747|PLMN_HUMAN Plasminogen OS = *Homo sapiens* GN = PLG PE = 1 SV = 2
>sp|P01860|IGHG3_HUMAN Ig gamma-3 chain C region OS = *Homo sapiens* GN = IGHG3
PE = 1 SV = 2
>sp|P0CG05|LAC2_HUMAN Ig lambda-2 chain C regions OS = *Homo sapiens* GN = IGLC2
PE = 1 SV = 1
>sp|P30626|SORCN_HUMAN Sorcin OS = *Homo sapiens* GN = SRI PE = 1 SV = 1
>sp|TRYP_PIG|(Common contaminant protein)
>sp|P02768|ALBU_HUMAN Serum albumin OS = *Homo sapiens* GN = ALB PE = 1 SV = 2
>sp|P04275|VWF_HUMAN von Willebrand factor OS = *Homo sapiens* GN = VWF PE = 1 SV = 4
>sp|Q12986|NFX1_HUMAN Transcriptional repressor NF-X1 OS = *Homo sapiens* GN = NFX1
PE = 1 SV = 2
>sp|HBB_HUMAN|(Common contaminant protein)
>sp|P11413|G6PD_HUMAN Glucose-6-phosphate 1-dehydrogenase OS = *Homo sapiens*
GN = G6PD PE = 1 SV = 4
>sp|P35269|T2FA_HUMAN General transcription factor IIF subunit 1 OS = *Homo sapiens*
GN = GTF2F1 PE = 1 SV = 2
>sp|O60814|H2B1K_HUMAN Histone H2B type 1-K OS = *Homo sapiens* GN = HIST1H2BK
PE = 1 SV = 3
>sp|P00488|F13A_HUMAN Coagulation factor XIII A chain OS = *Homo sapiens* GN = F13A1
PE = 1 SV = 4
>sp|P61978|HNRPK_HUMAN Heterogeneous nuclear ribonucleoprotein K OS = *Homo sapiens*
GN = HNRNPK PE = 1 SV = 1
>sp|Q8WUM4|PDC6I_HUMAN Programmed cell death 6-interacting protein OS = *Homo sapiens*
GN = PDCD6IP PE = 1 SV = 1
>sp|P60842|IF4A1_HUMAN Eukaryotic initiation factor 4A-I OS = *Homo sapiens* GN = EIF4A1
PE = 1 SV = 1
>sp|P11166|GTR1_HUMAN Solute carrier family 2, facilitated glucose transporter member 1
OS = *Homo sapiens* GN = SLC2A1 PE = 1 SV = 2
>sp|P30613|KPYR_HUMAN Pyruvate kinase PKLR OS = *Homo sapiens* GN = PKLR PE = 1 SV = 2
>sp|Q9Y490|TLN1_HUMAN Talin-1 OS = *Homo sapiens* GN = TLN1 PE = 1 SV = 3
>sp|P20073|ANXA7_HUMAN Annexin A7 OS = *Homo sapiens* GN = ANXA7 PE = 1 SV = 3
>sp|P01623|KV305_HUMAN Ig kappa chain V-III region WOL OS = *Homo sapiens* PE = 1 SV = 1
>sp|Q9Y6C2|EMIL1_HUMAN EMILIN-1 OS = *Homo sapiens* GN = EMILIN1 PE = 1 SV = 2
>sp|Q9UNZ2|NSF1C_HUMAN NSFL1 cofactor p47 OS = *Homo sapiens* GN = NSFL1C PE = 1
SV = 2
>sp|P68104|EF1A1_HUMAN Elongation factor 1-alpha 1 OS = *Homo sapiens* GN = EEF1A1
PE = 1 SV = 1
>sp|Q13404|UB2V1_HUMAN Ubiquitin-conjugating enzyme E2 variant 1 OS = *Homo sapiens*
GN = UBE2V1 PE = 1 SV = 2
>tr|A0A0B4J2B5|A0A0B4J2B5_HUMAN Protein IGHV3OR16-9 (Fragment) OS = *Homo sapiens*
GN = IGHV3OR16-9 PE = 1 SV = 1
>sp|P04083|ANXA1_HUMAN Annexin A1 OS = *Homo sapiens* GN = ANXA1 PE = 1 SV = 2
>sp|P08311|CATG_HUMAN Cathepsin G OS = *Homo sapiens* GN = CTSG PE = 1 SV = 2
>sp|P59665|DEF1_HUMAN Neutrophil defensin 1 OS = *Homo sapiens* GN = DEFA1 PE = 1 SV = 1

TABLE 1-continued protein list:

>sp|P13727|PRG2__HUMAN Bone marrow proteoglycan OS = Homo sapiens GN = PRG2 PE = 1 SV = 2
>sp|P35579|MYH9__HUMAN Myosin-9 OS = Homo sapiens GN = MYH9 PE = 1 SV = 4
>sp|P01009|A1AT__HUMAN Alpha-1-antitrypsin OS = Homo sapiens GN = SERPINA1 PE = 1 SV = 3
>sp|P12724|ECP__HUMAN Eosinophil cationic protein OS = Homo sapiens GN = RNASE3 PE = 1 SV = 2
>sp|P06727|APOA4__HUMAN Apolipoprotein A-IV OS = Homo sapiens GN = APOA4 PE = 1 SV = 3
>sp|P50570|DYN2__HUMAN Dynamin-2 OS = Homo sapiens GN = DNM2 PE = 1 SV = 2
>sp|P30043|BLVRB__HUMAN Flavin reductase (NADPH) OS = Homo sapiens GN = BLVRB PE = 1 SV = 3
>sp|Q14624|ITIH4__HUMAN Inter-alpha-trypsin inhibitor heavy chain H4 OS = Homo sapiens GN = ITIH4 PE = 1 SV = 4
>sp|Q15365|PCBP1__HUMAN Poly(rC)-binding protein 1 OS = Homo sapiens GN = PCBP1 PE = 1 SV = 2
>sp|P04264|K2C1__HUMAN Keratin, type II cytoskeletal 1 OS = Homo sapiens GN = KRT1 PE = 1 SV = 6
>sp|Q9Y3I1|FBX7__HUMAN F-box only protein 7 OS = Homo sapiens GN = FBXO7 PE = 1 SV = 1
>sp|P37840|SYUA__HUMAN Alpha-synuclein OS = Homo sapiens GN = SNCA PE = 1 SV = 1
>sp|Q7Z4W1|DCXR__HUMAN L-xylulose reductase OS = Homo sapiens GN = DCXR PE = 1 SV = 2
>sp|Q14847|LASP1__HUMAN LIM and SH3 domain protein 1 OS = Homo sapiens GN = LASP1 PE = 1 SV = 2
>sp|P31949|S10AB__HUMAN Protein S100-A11 OS = Homo sapiens GN = S100A11 PE = 1 SV = 2
>sp|P02649|APOE__HUMAN Apolipoprotein E OS = Homo sapiens GN = APOE PE = 1 SV = 1
>sp|P62805|H4__HUMAN Histone H4 OS = Homo sapiens GN = HIST1H4A PE = 1 SV = 2
>sp|Q16695|H31T__HUMAN Histone H3.1t OS = Homo sapiens GN = HIST3H3 PE = 1 SV = 3
>sp|P14543|NID1__HUMAN Nidogen-1 OS = Homo sapiens GN = NID1 PE = 1 SV = 3
>sp|P02788|TRFL__HUMAN Lactotransferrin OS = Homo sapiens GN = LTF PE = 1 SV = 6
>sp|P10909|CLUS__HUMAN Clusterin OS = Homo sapiens GN = CLU PE = 1 SV = 1
>sp|P11940|PABP1__HUMAN Polyadenylate-binding protein 1 OS = Homo sapiens GN = PABPC1 PE = 1 SV = 2
>sp|P49368|TCPG__HUMAN T-complex protein 1 subunit gamma OS = Homo sapiens GN = CCT3 PE = 1 SV = 4
>sp|P08758|ANXA5__HUMAN Annexin A5 OS = Homo sapiens GN = ANXA5 PE = 1 SV = 2
>sp|Q15691|MARE1__HUMAN Microtubule-associated protein RP/EB family member 1 OS = Homo sapiens GN = MAPRE1 PE = 1 SV = 3
>sp|P68363|TBA1B__HUMAN Tubulin alpha-1B chain OS = Homo sapiens GN = TUBA1B PE = 1 SV = 1
>sp|P0C0S8|H2A1__HUMAN Histone H2A type 1 OS = Homo sapiens GN = HIST1H2AG PE = 1 SV = 2
>sp|Q9UKV8|AGO2__HUMAN Protein argonaute-2 OS = Homo sapiens GN = AGO2 PE = 1 SV = 3
>sp|P12429|ANXA3__HUMAN Annexin A3 OS = Homo sapiens GN = ANXA3 PE = 1 SV = 3
>sp|P07996|TSP1__HUMAN Thrombospondin-1 OS = Homo sapiens GN = THBS1 PE = 1 SV = 2
>sp|Q562R1|ACTBL__HUMAN Beta-actin-like protein 2 OS = Homo sapiens GN = ACTBL2 PE = 1 SV = 2
>sp|P07437|TBB5__HUMAN Tubulin beta chain OS = Homo sapiens GN = TUBB PE = 1 SV = 2
>sp|O00233|PSMD9__HUMAN 26S proteasome non-ATPase regulatory subunit 9 OS = Homo sapiens GN = PSMD9 PE = 1 SV = 3
>sp|P05160|F13B__HUMAN Coagulation factor XIII B chain OS = Homo sapiens GN = F13B PE = 1 SV = 3
>sp|P62826|RAN__HUMAN GTP-binding nuclear protein Ran OS = Homo sapiens GN = RAN PE = 1 SV = 3
>tr|A0A087WZW8|A0A087WZW8__HUMAN Protein IGKV3-11 OS = Homo sapiens GN = IGKV3-11 PE = 4 SV = 1
>sp|P02452|CO1A1__HUMAN Collagen alpha-1(I) chain OS = Homo sapiens GN = COL1A1 PE = 1 SV = 5
>sp|Q9GZP4|PITH1__HUMAN PITH domain-containing protein 1 OS = Homo sapiens GN = PITHD1 PE = 1 SV = 1
>sp|Q14766|LTBP1__HUMAN Latent-transforming growth factor beta-binding protein 1 OS = Homo sapiens GN = LTBP1 PE = 1 SV = 4
>sp|Q9UJU6|DBNL__HUMAN Drebrin-like protein OS = Homo sapiens GN = DBNL PE = 1 SV = 1
>sp|P02747|C1QC__HUMAN Complement C1q subcomponent subunit C OS = Homo sapiens GN = C1QC PE = 1 SV = 3
>sp|P26447|S10A4__HUMAN Protein S100-A4 OS = Homo sapiens GN = S100A4 PE = 1 SV = 1
>sp|P08133|ANXA6__HUMAN Annexin A6 OS = Homo sapiens GN = ANXA6 PE = 1 SV = 3
>sp|Q14254|FLOT2__HUMAN Flotillin-2 OS = Homo sapiens GN = FLOT2 PE = 1 SV = 2
>sp|P03952|KLKB1__HUMAN Plasma kallikrein OS = Homo sapiens GN = KLKB1 PE = 1 SV = 1
>sp|P06753|TPM3__HUMAN Tropomyosin alpha-3 chain OS = Homo sapiens GN = TPM3 PE = 1 SV = 2
>sp|P35580|MYH10__HUMAN Myosin-10 OS = Homo sapiens GN = MYH10 PE = 1 SV = 3
>sp|P17987|TCPA__HUMAN T-complex protein 1 subunit alpha OS = Homo sapiens GN = TCP1 PE = 1 SV = 1
>sp|P04040|CATA__HUMAN Catalase OS = Homo sapiens GN = CAT PE = 1 SV = 3
>sp|P32119|PRDX2__HUMAN Peroxiredoxin-2 OS = Homo sapiens GN = PRDX2 PE = 1 SV = 5
>sp|P02746|C1QB__HUMAN Complement C1q subcomponent subunit B OS = Homo sapiens GN = C1QB PE = 1 SV = 3

TABLE 1-continued protein list:

>tr|J3QRK5|J3QRK5_HUMAN Protein UBBP4 OS = *Homo sapiens* GN = UBBP4 PE = 1 SV = 1
>sp|Q15582|BGH3_HUMAN Transforming growth factor-beta-induced protein ig-h3 OS = *Homo sapiens* GN = TGFBI PE = 1 SV = 1
>sp|P13645|K1C10_HUMAN Keratin, type I cytoskeletal 10 OS = *Homo sapiens* GN = KRT10 PE = 1 SV = 6
>sp|P21333|FLNA_HUMAN Filamin-A OS = *Homo sapiens* GN = FLNA PE = 1 SV = 4
>sp|P37802|TAGL2_HUMAN Transgelin-2 OS = *Homo sapiens* GN = TAGLN2 PE = 1 SV = 3
>sp|Q5TDH0|DDI2_HUMAN Protein DDI1 homolog 2 OS = *Homo sapiens* GN = DDI2 PE = 1 SV = 1
>sp|P04004|VTNC_HUMAN Vitronectin OS = *Homo sapiens* GN = VTN PE = 1 SV = 1
>sp|Q5XPI4|RN123_HUMAN E3 ubiquitin-protein ligase RNF123 OS = *Homo sapiens* GN = RNF123 PE = 1 SV = 1
>sp|P02652|APOA2_HUMAN Apolipoprotein A-II OS = *Homo sapiens* GN = APOA2 PE = 1 SV = 1
>sp|P02549|SPTA1_HUMAN Spectrin alpha chain, erythrocytic 1 OS = *Homo sapiens* GN = SPTA1 PE = 1 SV = 5
>sp|P01871|IGHM_HUMAN Ig mu chain C region OS = *Homo sapiens* GN = IGHM PE = 1 SV = 3
>sp|Q9Y2V2|CHSP1_HUMAN Calcium-regulated heat stable protein 1 OS = *Homo sapiens* GN = CARHSP1 PE = 1 SV = 2
>sp|Q96CW1|AP2M1_HUMAN AP-2 complex subunit mu OS = *Homo sapiens* GN = AP2M1 PE = 1 SV = 2
>sp|P50991|TCPD_HUMAN T-complex protein 1 subunit delta OS = *Homo sapiens* GN = CCT4 PE = 1 SV = 4
>sp|Q6B0K9|HBM_HUMAN Hemoglobin subunit mu OS = *Homo sapiens* GN = HBM PE = 2 SV = 1
>sp|P26599|PTBP1_HUMAN Polypyrimidine tract-binding protein 1 OS = *Homo sapiens* GN = PTBP1 PE = 1 SV = 1
>sp|P04406|G3P_HUMAN Glyceraldehyde-3-phosphate dehydrogenase OS = *Homo sapiens* GN = GAPDH PE = 1 SV = 3
>sp|P00568|KAD1_HUMAN Adenylate kinase isoenzyme 1 OS = *Homo sapiens* GN = AK1 PE = 1 SV = 3
>sp|Q9Y2Y8|PRG3_HUMAN Proteoglycan 3 OS = *Homo sapiens* GN = PRG3 PE = 1 SV = 2
>sp|Q5T4S7|UBR4_HUMAN E3 ubiquitin-protein ligase UBR4 OS = *Homo sapiens* GN = UBR4 PE = 1 SV = 1
>sp|Q00610|CLH1_HUMAN Clathrin heavy chain 1 OS = *Homo sapiens* GN = CLTC PE = 1 SV = 5
>sp|P30041|PRDX6_HUMAN Peroxiredoxin-6 OS = *Homo sapiens* GN = PRDX6 PE = 1 SV = 3
>sp|P16671|CD36_HUMAN Platelet glycoprotein 4 OS = *Homo sapiens* GN = CD36 PE = 1 SV = 2
>sp|P50995|ANX11_HUMAN Annexin A11 OS = *Homo sapiens* GN = ANXA11 PE = 1 SV = 1
>sp|Q04637|IF4G1_HUMAN Eukaryotic translation initiation factor 4 gamma 1 OS = Homo sapiens GN = EIF4G1 PE = 1 SV = 4
>sp|O75131|CPNE3_HUMAN Copine-3 OS = *Homo sapiens* GN = CPNE3 PE = 1 SV = 1
>sp|P16157|ANK1_HUMAN Ankyrin-1 OS = *Homo sapiens* GN = ANK1 PE = 1 SV = 3
>sp|Q01518|CAP1_HUMAN Adenylyl cyclase-associated protein 1 OS = *Homo sapiens* GN = CAP1 PE = 1 SV = 5
>sp|P16401|H15_HUMAN Histone H1.5 OS = *Homo sapiens* GN = HIST1H1B PE = 1 SV = 3
>sp|P01593|KV101_HUMAN Ig kappa chain V-I region AG OS = *Homo sapiens* PE = 1 SV = 1
>sp|Q99832|TCPH_HUMAN T-complex protein 1 subunit eta OS = *Homo sapiens* GN = CCT7 PE = 1 SV = 2
>sp|P19823|ITIH2_HUMAN Inter-alpha-trypsin inhibitor heavy chain H2 OS = *Homo sapiens* GN = ITIH2 PE = 1 SV = 2
>sp|P53004|BIEA_HUMAN Biliverdin reductase A OS = *Homo sapiens* GN = BLVRA PE = 1 SV = 2
>sp|P01617|KV204_HUMAN Ig kappa chain V-II region TEW OS = *Homo sapiens* PE = 1 SV = 1
>sp|P00390|GSHR_HUMAN Glutathione reductase, mitochondrial OS = *Homo sapiens* GN = GSR PE = 1 SV = 2
>sp|P54727|RD23B_HUMAN UV excision repair protein RAD23 homolog B OS = *Homo sapiens* GN = RAD23B PE = 1 SV = 1
>sp|Q93008|USP9X_HUMAN Probable ubiquitin carboxyl-terminal hydrolase FAF-X OS = *Homo sapiens* GN = USP9X PE = 1 SV = 3
>sp|Q02086|SP2_HUMAN Transcription factor Sp2 OS = *Homo sapiens* GN = SP2 PE = 1 SV = 3
>sp|P31943|HNRH1_HUMAN Heterogeneous nuclear ribonucleoprotein H OS = *Homo sapiens* GN = HNRNPH1 PE = 1 SV = 4
>sp|P23588|IF4B_HUMAN Eukaryotic translation initiation factor 4B OS = *Homo sapiens* GN = EIF4B PE = 1 SV = 2
>sp|P04196|HRG_HUMAN Histidine-rich glycoprotein OS = *Homo sapiens* GN = HRG PE = 1 SV = 1
>sp|P98160|PGBM_HUMAN Basement membrane-specific heparan sulfate proteoglycan core protein OS = *Homo sapiens* GN = HSPG2 PE = 1 SV = 4
>sp|Q9NTK5|OLA1_HUMAN Obg-like ATPase 1 OS = *Homo sapiens* GN = OLA1 PE = 1 SV = 2
>sp|Q9BUF5|TBB6_HUMAN Tubulin beta-6 chain OS = *Homo sapiens* GN = TUBB6 PE = 1 SV = 1
>tr|A0A0B4J1T9|A0A0B4J1T9_HUMAN Protein IGKV3-15 (Fragment) OS = *Homo sapiens* GN = IGKV3-15 PE = 4 SV = 1
>sp|P25685|DNJB1_HUMAN DnaJ homolog subfamily B member 1 OS = *Homo sapiens* GN = DNAJB1 PE = 1 SV = 4
>sp|O43665|RGS10_HUMAN Regulator of G-protein signaling 10 OS = *Homo sapiens* GN = RGS10 PE = 1 SV = 2
>sp|Q06124|PTN11_HUMAN Tyrosine-protein phosphatase non-receptor type 11 OS = *Homo sapiens* GN = PTPN11 PE = 1 SV = 2

TABLE 1-continued protein list:

>sp|P00734|THRB_HUMAN Prothrombin OS = Homo sapiens GN = F2 PE = 1 SV = 2
>sp|O14964|HGS_HUMAN Hepatocyte growth factor-regulated tyrosine kinase substrate
OS = Homo sapiens GN = HGS PE = 1 SV = 1
>sp|Q16610|ECM1_HUMAN Extracellular matrix protein 1 OS = Homo sapiens GN = ECM1
PE = 1 SV = 2
>sp|Q08722|CD47_HUMAN Leukocyte surface antigen CD47 OS = Homo sapiens GN = CD47
PE = 1 SV = 1
>sp|P15153|RAC2_HUMAN Ras-related C3 botulinum toxin substrate 2 OS = Homo sapiens
GN = RAC2 PE = 1 SV = 1
>sp|P10412|H14_HUMAN Histone H1.4 OS = Homo sapiens GN = HIST1H1E PE = 1 SV = 2
>sp|P12111|CO6A3_HUMAN Collagen alpha-3(VI) chain OS = Homo sapiens GN = COL6A3
PE = 1 SV = 5
>tr|H3BM21|H3BM21_HUMAN Integrin beta (Fragment) OS = Homo sapiens PE = 3 SV = 1
>sp|B9A064|IGLL5_HUMAN Immunoglobulin lambda-like polypeptide 5 OS = Homo sapiens
GN = IGLL5 PE = 2 SV = 2
>sp|P08246|ELNE_HUMAN Neutrophil elastase OS = Homo sapiens GN = ELANE PE = 1 SV = 1
>sp|P01859|IGHG2_HUMAN Ig gamma-2 chain C region OS = Homo sapiens GN = IGHG2
PE = 1 SV = 2
>sp|P61626|LYSC_HUMAN Lysozyme C OS = Homo sapiens GN = LYZ PE = 1 SV = 1
>sp|Q9UQ80|PA2G4_HUMAN Proliferation-associated protein 2G4 OS = Homo sapiens
GN = PA2G4 PE = 1 SV = 3
>sp|P22626|ROA2_HUMAN Heterogeneous nuclear ribonucleoproteins A2/B1
OS = Homo sapiens GN = HNRNPA2B1 PE = 1 SV = 2
>sp|P01621|KV303_HUMAN Ig kappa chain V-III region NG9 (Fragment) OS = Homo sapiens
PE = 1 SV = 1
>sp|P11171|41_HUMAN Protein 4.1 OS = Homo sapiens GN = EPB41 PE = 1 SV = 4
>sp|P63241|IF5A1_HUMAN Eukaryotic translation initiation factor 5A-1 OS = Homo sapiens
GN = EIF5A PE = 1 SV = 2
>sp|Q14247|SRC8_HUMAN Src substrate cortactin OS = Homo sapiens GN = CTTN PE = 1 SV = 2
>sp|P07355|ANXA2_HUMAN Annexin A2 OS = Homo sapiens GN = ANXA2 PE = 1 SV = 2
>sp|P01598|KV106_HUMAN Ig kappa chain V-I region EU OS = Homo sapiens PE = 1 SV = 1
>sp|O75955|FLOT1_HUMAN Flotillin-1 OS = Homo sapiens GN = FLOT1 PE = 1 SV = 3
>sp|P35908|K22E_HUMAN Keratin, type II cytoskeletal 2 epidermal OS = Homo sapiens
GN = KRT2 PE = 1 SV = 2
>sp|Q06830|PRDX1_HUMAN Peroxiredoxin-1 OS = Homo sapiens GN = PRDX1 PE = 1 SV = 1
>sp|P01625|KV402_HUMAN Ig kappa chain V-IV region Len OS = Homo sapiens PE = 1 SV = 2
>sp|P01042|KNG1_HUMAN Kininogen-1 OS = Homo sapiens GN = KNG1 PE = 1 SV = 2
>sp|Q86UX7|URP2_HUMAN Fermitin family homolog 3 OS = Homo sapiens GN = FERMT3
PE = 1 SV = 1
>tr|A6NE09|A6NE09_HUMAN 40S ribosomal protein SA OS = Homo sapiens GN = RPSAP58
PE = 1 SV = 1
>sp|Q9BSL1|UBAC1_HUMAN Ubiquitin-associated domain-containing protein 1
OS = Homo sapiens GN = UBAC1 PE = 1 SV = 1
>sp|P09651|ROA1_HUMAN Heterogeneous nuclear ribonucleoprotein A1 OS = Homo sapiens
GN = HNRNPA1 PE = 1 SV = 5
>sp|Q9H169|STMN4_HUMAN Stathmin-4 OS = Homo sapiens GN = STMN4 PE = 2 SV = 1
>sp|P20160|CAP7_HUMAN Azurocidin OS = Homo sapiens GN = AZU1 PE = 1 SV = 3
>sp|P16452|EPB42_HUMAN Erythrocyte membrane protein band 4.2 OS = Homo sapiens
GN = EPB42 PE = 1 SV = 3
>sp|Q9UIA9|XPO7_HUMAN Exportin-7 OS = Homo sapiens GN = XPO7 PE = 1 SV = 3
>sp|O95747|OXSR1_HUMAN Serine/threonine-protein kinase OSR1 OS = Homo sapiens
GN = OXSR1 PE = 1 SV = 1
>sp|P52294|IMA5_HUMAN Importin subunit alpha-5 OS = Homo sapiens GN = KPNA1
PE = 1 SV = 3
>sp|Q14974|IMB1_HUMAN Importin subunit beta-1 OS = Homo sapiens GN = KPNB1 PE = 1
SV = 2
>sp|P02008|HBAZ_HUMAN Hemoglobin subunit zeta OS = Homo sapiens GN = HBZ PE = 1
SV = 2
>sp|P23528|COF1_HUMAN Cofilin-1 OS = Homo sapiens GN = CFL1 PE = 1 SV = 3
>tr|A0A075B6R2|A0A075B6R2_HUMAN Protein IGHV4-4 (Fragment) OS = Homo sapiens
GN = IGHV4-4 PE = 4 SV = 2
>sp|P06310|KV206_HUMAN Ig kappa chain V-II region RPMI 6410 OS = Homo sapiens
PE = 4 SV = 1
>sp|P16403|H12_HUMAN Histone H1.2 OS = Homo sapiens GN = HIST1H1C PE = 1 SV = 2
>sp|P05107|ITB2_HUMAN Integrin beta-2 OS = Homo sapiens GN = ITGB2 PE = 1 SV = 2
>sp|P02647|APOA1_HUMAN Apolipoprotein A-I OS = Homo sapiens GN = APOA1 PE = 1
SV = 1
>sp|Q16401|PSMD5_HUMAN 26S proteasome non-ATPase regulatory subunit 5
OS = Homo sapiens GN = PSMD5 PE = 1 SV = 3
>sp|Q16204|CCDC6_HUMAN Coiled-coil domain-containing protein 6 OS = Homo sapiens
GN = CCDC6 PE = 1 SV = 2
>sp|Q86VP6|CAND1_HUMAN Cullin-associated NEDD8-dissociated protein 1
OS = Homo sapiens GN = CAND1 PE = 1 SV = 2
>sp|P34932|HSP74_HUMAN Heat shock 70 kDa protein 4 OS = Homo sapiens GN = HSPA4
PE = 1 SV = 4
>sp|Q5VVQ6|OTU1_HUMAN Ubiquitin thioesterase OTU1 OS = Homo sapiens GN = YOD1
PE = 1 SV = 1

TABLE 1-continued protein list:

>sp|Q7LBR1|CHM1B_HUMAN Charged multivesicular body protein 1b OS = Homo sapiens
GN = CHMP1B PE = 1 SV = 1
>sp|Q9BY43|CHM4A_HUMAN Charged multivesicular body protein 4a OS = Homo sapiens
GN = CHMP4A PE = 1 SV = 3
>sp|Q9BSK4|FEM1A_HUMAN Protein fem-1 homolog A OS = Homo sapiens GN = FEM1A
PE = 1 SV = 1
>sp|P08107|HSP71_HUMAN Heat shock 70 kDa protein 1A/1B OS = Homo sapiens
GN = HSPA1A PE = 1 SV = 5
>sp|P01603|KV111_HUMAN Ig kappa chain V-I region Ka OS = Homo sapiens PE = 1 SV = 1
>sp|P11142|HSP7C_HUMAN Heat shock cognate 71 kDa protein OS = Homo sapiens
GN = HSPA8 PE = 1 SV = 1
>sp|P02745|C1QA_HUMAN Complement C1q subcomponent subunit A OS = Homo sapiens
GN = C1QA PE = 1 SV = 2
>tr|F5H423|F5H423_HUMAN Uncharacterized protein OS = Homo sapiens PE = 3 SV = 1
>sp|P50552|VASP_HUMAN Vasodilator-stimulated phosphoprotein OS = Homo sapiens
GN = VASP PE = 1 SV = 3
>sp|Q00013|EM55_HUMAN 55 kDa erythrocyte membrane protein OS = Homo sapiens
GN = MPP1 PE = 1 SV = 2
>tr|A0A0B4J1U2|A0A0B4J1U2_HUMAN Protein IGLV7-43 (Fragment) OS = Homo sapiens
GN = IGLV7-43 PE = 4 SV = 1
>sp|O00410|IPO5_HUMAN Importin-5 OS = Homo sapiens GN = IPO5 PE = 1 SV = 4
>tr|A0A0B4J1Z7|A0A0B4J1Z7_HUMAN Protein IGKV1-39 (Fragment) OS = Homo sapiens
GN = IGKV1-39 PE = 1 SV = 1
>sp|P08603|CFAH_HUMAN Complement factor H OS = Homo sapiens GN = CFH PE = 1 SV = 4
>sp|Q10567|AP1B1_HUMAN AP-1 complex subunit beta-1 OS = Homo sapiens GN = AP1B1
PE = 1 SV = 2
>sp|Q04323|UBXN1_HUMAN UBX domain-containing protein 1 OS = Homo sapiens
GN = UBXN1 PE = 1 SV = 2
>sp|Q9NRW1|RAB6B_HUMAN Ras-related protein Rab-6B OS = Homo sapiens GN = RAB6B
PE = 1 SV = 1
>sp|P11169|GTR3_HUMAN Solute carrier family 2, facilitated glucose transporter member 3
OS = Homo sapiens GN = SLC2A3 PE = 1 SV = 1
>sp|P15311|EZRI_HUMAN Ezrin OS = Homo sapiens GN = EZR PE = 1 SV = 4
>sp|P13796|PLSL_HUMAN Plastin-2 OS = Homo sapiens GN = LCP1 PE = 1 SV = 6
>sp|P46734|MP2K3_HUMAN Dual specificity mitogen-activated protein kinase kinase 3
OS = Homo sapiens GN = MAP2K3 PE = 1 SV = 2
>tr|A0A075B6I0|A0A075B6I0_HUMAN Protein IGLV8-61 (Fragment) OS = Homo sapiens
GN = IGLV8-61 PE = 1 SV = 3
>sp|Q9H4A3|WNK1_HUMAN Serine/threonine-protein kinase WNK1 OS = Homo sapiens
GN = WNK1 PE = 1 SV = 2
>sp|P08670|VIME_HUMAN Vimentin OS = Homo sapiens GN = VIM PE = 1 SV = 4
>sp|P05546|HEP2_HUMAN Heparin cofactor 2 OS = Homo sapiens GN = SERPIND1 PE = 1 SV = 3
>sp|Q9Y277|VDAC3_HUMAN Voltage-dependent anion-selective channel protein 3
OS = Homo sapiens GN = VDAC3 PE = 1 SV = 1
>sp|P01765|HV304_HUMAN Ig heavy chain V-III region TIL OS = Homo sapiens PE = 1 SV = 1
>sp|O14578|CTRO_HUMAN Citron Rho-interacting kinase OS = Homo sapiens GN = CIT
PE = 1 SV = 2
>sp|Q9UBV8|PEF1_HUMAN Peflin OS = Homo sapiens GN = PEF1 PE = 1 SV = 1
>sp|O95782|AP2A1_HUMAN AP-2 complex subunit alpha-1 OS = Homo sapiens GN = AP2A1
PE = 1 SV = 3
>sp|P02775|CXCL7_HUMAN Platelet basic protein OS = Homo sapiens GN = PPBP PE = 1 SV = 3
>sp|P16050|LOX15_HUMAN Arachidonate 15-lipoxygenase OS = Homo sapiens GN = ALOX15
PE = 1 SV = 3
>sp|P01616|KV203_HUMAN Ig kappa chain V-II region MIL OS = Homo sapiens PE = 1 SV = 1
>sp|P04075|ALDOA_HUMAN Fructose-bisphosphate aldolase A OS = Homo sapiens
GN = ALDOA PE = 1 SV = 2
>sp|Q15819|UB2V2_HUMAN Ubiquitin-conjugating enzyme E2 variant 2 OS = Homo sapiens
GN = UBE2V2 PE = 1 SV = 4
>sp|Q9Y570|PPME1_HUMAN Protein phosphatase methylesterase 1 OS = Homo sapiens
GN = PPME1 PE = 1 SV = 3
>sp|Q8WW22|DNJA4_HUMAN DnaJ homolog subfamily A member 4 OS = Homo sapiens
GN = DNAJA4 PE = 1 SV = 1
>sp|P01137|TGFB1_HUMAN Transforming growth factor beta-1 OS = Homo sapiens
GN = TGFB1 PE = 1 SV = 2
>sp|P84095|RHOG_HUMAN Rho-related GTP-binding protein RhoG OS = Homo sapiens
GN = RHOG PE = 1 SV = 1
>sp|P80511|S10AC_HUMAN Protein S100-A12 OS = Homo sapiens GN = S100A12 PE = 1 SV = 2
>sp|Q9H0U4|RAB1B_HUMAN Ras-related protein Rab-1B OS = Homo sapiens GN = RAB1B
PE = 1 SV = 1
>sp|Q93084|AT2A3_HUMAN Sarcoplasmic/endoplasmic reticulum calcium ATPase 3
OS = Homo sapiens GN = ATP2A3 PE = 1 SV = 2
>sp|P09496|CLCA_HUMAN Clathrin light chain A OS = Homo sapiens GN = CLTA PE = 1 SV = 1
>sp|P20292|AL5AP_HUMAN Arachidonate 5-lipoxygenase-activating protein OS = Homo
sapiens GN = ALOX5AP PE = 1 SV = 2
>sp|Q96EP5|DAZP1_HUMAN DAZ-associated protein 1 OS = Homo sapiens GN = DAZAP1
PE = 1 SV = 1
>tr|A0A0C4DH35|A0A0C4DH35_HUMAN Protein IGHV3-35 (Fragment) OS = Homo sapiens
GN = IGHV3-35 PE = 4 SV = 1

TABLE 1-continued protein list:

>sp|Q96NA2|RILP_HUMAN Rab-interacting lysosomal protein OS = Homo sapiens GN = RILP PE = 1 SV = 1
>sp|P04839|CY24B_HUMAN Cytochrome b-245 heavy chain OS = Homo sapiens GN = CYBB PE = 1 SV = 2
>sp|Q9Y265|RUVB1_HUMAN RuvB-like 1 OS = Homo sapiens GN = RUVBL1 PE = 1 SV = 1
>sp|Q02161|RHD_HUMAN Blood group Rh(D) polypeptide OS = Homo sapiens GN = RHD PE = 1 SV = 3
>sp|P48507|GSH0_HUMAN Glutamate--cysteine ligase regulatory subunit OS = Homo sapiens GN = GCLM PE = 1 SV = 1
>tr|A0A0B4J2B7|A0A0B4J2B7_HUMAN Protein IGHV3-30 (Fragment) OS = Homo sapiens GN = IGHV3-30 PE = 1 SV = 1
>sp|P45880|VDAC2_HUMAN Voltage-dependent anion-selective channel protein 2 OS = Homo sapiens GN = VDAC2 PE = 1 SV = 2
>sp|Q86XH1|IQCA1_HUMAN IQ and AAA domain-containing protein 1 OS = Homo sapiens GN = IQCA1 PE = 2 SV = 1
>sp|P08962|CD63_HUMAN CD63 antigen OS = Homo sapiens GN = CD63 PE = 1 SV = 2
>tr|A0A0B4J1U7|A0A0B4J1U7_HUMAN Protein IGHV6-1 (Fragment) OS = Homo sapiens GN = IGHV6-1 PE = 4 SV = 1
>sp|P46109|CRKL_HUMAN Crk-like protein OS = Homo sapiens GN = CRKL PE = 1 SV = 1
>sp|Q12805|FBLN3_HUMAN EGF-containing fibulin-like extracellular matrix protein 1 OS = Homo sapiens GN = EFEMP1 PE = 1 SV = 2
>sp|P04921|GLPC_HUMAN Glycophorin-C OS = Homo sapiens GN = GYPC PE = 1 SV = 1
>sp|P01019|ANGT_HUMAN Angiotensinogen OS = Homo sapiens GN = AGT PE = 1 SV = 1
>sp|P05155|IC1_HUMAN Plasma protease C1 inhibitor OS = Homo sapiens GN = SERPING1 PE = 1 SV = 2
>sp|P09525|ANXA4_HUMAN Annexin A4 OS = Homo sapiens GN = ANXA4 PE = 1 SV = 4
>sp|Q06033|ITIH3_HUMAN Inter-alpha-trypsin inhibitor heavy chain H3 OS = Homo sapiens GN = ITIH3 PE = 1 SV = 2
>tr|A0A075B6J7|A0A075B6J7_HUMAN Protein IGLV3-21 (Fragment) OS = Homo sapiens GN = IGLV3-21 PE = 1 SV = 1
>sp|P53396|ACLY_HUMAN ATP-citrate synthase OS = Homo sapiens GN = ACLY PE = 1 SV = 3
>sp|P51692|STA5B_HUMAN Signal transducer and activator of transcription 5B OS = Homo sapiens GN = STAT5B PE = 1 SV = 2
>sp|P62330|ARF6_HUMAN ADP-ribosylation factor 6 OS = Homo sapiens GN = ARF6 PE = 1 SV = 2
>sp|P25686|DNJB2_HUMAN DnaJ homolog subfamily B member 2 OS = Homo sapiens GN = DNAJB2 PE = 1 SV = 3
>tr|K7N7A8|K7N7A8_HUMAN Uncharacterized protein (Fragment) OS = Homo sapiens PE = 3 SV = 2
>sp|Q13418|ILK_HUMAN Integrin-linked protein kinase OS = Homo sapiens GN = ILK PE = 1 SV = 2
>sp|Q9NP79|VTA1_HUMAN Vacuolar protein sorting-associated protein VTA1 homolog OS = Homo sapiens GN = VTA1 PE = 1 SV = 1
>sp|Q16181|SEPT7_HUMAN Septin-7 OS = Homo sapiens GN = SEPT7 PE = 1 SV = 2
>sp|P04208|LV106_HUMAN Ig lambda chain V-I region WAH OS = Homo sapiens PE = 1 SV = 1
>sp|O14980|XPO1_HUMAN Exportin-1 OS = Homo sapiens GN = XPO1 PE = 1 SV = 1
>sp|Q13057|COASY_HUMAN Bifunctional coenzyme A synthase OS = Homo sapiens GN = COASY PE = 1 SV = 4
>sp|Q13526|PIN1_HUMAN Peptidyl-prolyl cis-trans isomerase NIMA-interacting 1 OS = Homo sapiens GN = PIN1 PE = 1 SV = 1
>sp|P54725|RD23A_HUMAN UV excision repair protein RAD23 homolog A OS = Homo sapiens GN = RAD23A PE = 1 SV = 1
>sp|O60784|TOM1_HUMAN Target of Myb protein 1 OS = Homo sapiens GN = TOM1 PE = 1 SV = 2
>sp|O43598|DNPH1_HUMAN 2'-deoxynucleoside 5'-phosphate N-hydrolase 1 OS = Homo sapiens GN = DNPH1 PE = 1 SV = 1
>sp|P40227|TCPZ_HUMAN T-complex protein 1 subunit zeta OS = Homo sapiens GN = CCT6A PE = 1 SV = 3
>sp|P21796|VDAC1_HUMAN Voltage-dependent anion-selective channel protein 1 OS = Homo sapiens GN = VDAC1 PE = 1 SV = 2
>sp|P07737|PROF1_HUMAN Profilin-1 OS = Homo sapiens GN = PFN1 PE = 1 SV = 2
>sp|P01761|HV106_HUMAN Ig heavy chain V-I region SIE OS = Homo sapiens PE = 1 SV = 1
>sp|Q16543|CDC37_HUMAN Hsp90 co-chaperone Cdc37 OS = Homo sapiens GN = CDC37 PE = 1 SV = 1
>sp|P78371|TCPB_HUMAN T-complex protein 1 subunit beta OS = Homo sapiens GN = CCT2 PE = 1 SV = 4
>sp|Q15942|ZYX_HUMAN Zyxin OS = Homo sapiens GN = ZYX PE = 1 SV = 1
>sp|P78318|IGBP1_HUMAN Immunoglobulin-binding protein 1 OS = Homo sapiens GN = IGBP1 PE = 1 SV = 1
>sp|P61020|RAB5B_HUMAN Ras-related protein Rab-5B OS = Homo sapiens GN = RAB5B PE = 1 SV = 1
>sp|P28676|GRAN_HUMAN Grancalcin OS = Homo sapiens GN = GCA PE = 1 SV = 2
>sp|P19827|ITIH1_HUMAN Inter-alpha-trypsin inhibitor heavy chain H1 OS = Homo sapiens GN = ITIH1 PE = 1 SV = 3

TABLE 1-continued protein list:

\>sp|P01608|KV116_HUMAN Ig kappa chain V-I region Roy OS = *Homo sapiens* PE = 1 SV = 1
\>sp|Q96P70|IPO9_HUMAN Importin-9 OS = *Homo sapiens* GN = IPO9 PE = 1 SV = 3
\>sp|Q00577|PURA_HUMAN Transcriptional activator protein Pur-alpha OS = *Homo sapiens* GN = PURA PE = 1 SV = 2
\>sp|P0C0L5|CO4B_HUMAN Complement C4-B OS = *Homo sapiens* GN = C4B PE = 1 SV = 2
\>sp|Q15435|PP1R7_HUMAN Protein phosphatase 1 regulatory subunit 7 OS = *Homo sapiens* GN = PPP1R7 PE = 1 SV = 1
\>sp|P08631|HCK_HUMAN Tyrosine-protein kinase HCK OS = *Homo sapiens* GN = HCK PE = 1 SV = 5
\>sp|P31942|HNRH3_HUMAN Heterogeneous nuclear ribonucleoprotein H3 OS = *Homo sapiens* GN = HNRNPH3 PE = 1 SV = 2
\>sp|Q5JTV8|TOIP1_HUMAN Torsin-1A-interacting protein 1 OS = *Homo sapiens* GN = TOR1AIP1 PE = 1 SV = 2
\>sp|Q92599|SEPT8_HUMAN Septin-8 OS = *Homo sapiens* GN = SEPT8 PE = 1 SV = 4
\>sp|P18206|VINC_HUMAN Vinculin OS = *Homo sapiens* GN = VCL PE = 1 SV = 4
\>sp|P54578|UBP14_HUMAN Ubiquitin carboxyl-terminal hydrolase 14 OS = *Homo sapiens* GN = USP14 PE = 1 SV = 3
\>sp|Q96CV9|OPTN_HUMAN Optineurin OS = *Homo sapiens* GN = OPTN PE = 1 SV = 2
\>sp|Q16555|DPYL2_HUMAN Dihydropyrimidinase-related protein 2 OS = *Homo sapiens* GN = DPYSL2 PE = 1 SV = 1
\>sp|Q92841|DDX17_HUMAN Probable ATP-dependent RNA helicase DDX17 OS = *Homo sapiens* GN = DDX17 PE = 1 SV = 2
\>sp|P52565|GDIR1_HUMAN Rho GDP-dissociation inhibitor 1 OS = *Homo sapiens* GN = ARHGDIA PE = 1 SV = 3
\>sp|P62736|ACTA_HUMAN Actin, aortic smooth muscle OS = *Homo sapiens* GN = ACTA2 PE = 1 SV = 1
\>sp|P68366|TBA4A_HUMAN Tubulin alpha-4A chain OS = *Homo sapiens* GN = TUBA4A PE = 1 SV = 1
\>sp|O00148|DX39A_HUMAN ATP-dependent RNA helicase DDX39A OS = *Homo sapiens* GN = DDX39A PE = 1 SV = 2
\>sp|P17213|BPI_HUMAN Bactericidal permeability-increasing protein OS = *Homo sapiens* GN = BPI PE = 1 SV = 4
\>sp|O15198|SMAD9_HUMAN Mothers against decapentaplegic homolog 9 OS = Homo sapiens GN = SMAD9 PE = 1 SV = 1
\>sp|Q99969|RARR2_HUMAN Retinoic acid receptor responder protein 2 OS = Homo sapiens GN = RARRES2 PE = 1 SV = 1
\>sp|Q8IXQ3|CI040_HUMAN Uncharacterized protein C9orf40 OS = *Homo sapiens* GN = C9orf40 PE = 1 SV = 1
\>sp|P04003|C4BPA_HUMAN C4b-binding protein alpha chain OS = *Homo sapiens* GN = C4BPA PE = 1 SV = 2
\>sp|P29622|KAIN_HUMAN Kallistatin OS = *Homo sapiens* GN = SERPINA4 PE = 1 SV = 3
\>sp|Q08380|LG3BP_HUMAN Galectin-3-binding protein OS = *Homo sapiens* GN = LGALS3BP PE = 1 SV = 1
\>sp|P09917|LOX5_HUMAN Arachidonate 5-lipoxygenase OS = *Homo sapiens* GN = ALOX5 PE = 1 SV = 2
\>sp|P17066|HSP76_HUMAN Heat shock 70 kDa protein 6 OS = *Homo sapiens* GN = HSPA6 PE = 1 SV = 2
\>sp|O00299|CLIC1_HUMAN Chloride intracellular channel protein 1 OS = *Homo sapiens* GN = CLIC1 PE = 1 SV = 4
\>sp|Q15366|PCBP2_HUMAN Poly(rC)-binding protein 2 OS = *Homo sapiens* GN = PCBP2 PE = 1 SV = 1
\>sp|P00403|COX2_HUMAN Cytochrome c oxidase subunit 2 OS = *Homo sapiens* GN = MT-CO2 PE = 1 SV = 1
\>sp|Q9Y6C9|MTCH2_HUMAN Mitochondrial carrier homolog 2 OS = *Homo sapiens* GN = MTCH2 PE = 1 SV = 1
\>sp|Q86YZ3|HORN_HUMAN Hornerin OS = *Homo sapiens* GN = HRNR PE = 1 SV = 2
\>sp|Q06187|BTK_HUMAN Tyrosine-protein kinase BTK OS = *Homo sapiens* GN = BTK PE = 1 SV = 3

Of the identified proteins, fibrinogen alpha and beta chains were confirmed not to include the Fp(A) and Fp(B) peptides, respectively, indicating the identified fibrinogen protein underwent thrombin-mediated cleavage and converted into insoluble fibrin.

Pathway enrichment analysis was performed using Reactome [PMID 24243840, 24213504] using a Uniprot accession list. Data was filtered using 1% FDR.

As shown in Table 2 which shows the Pathway enrichment, a total of 65 pathways were identified. Most of these identified pathways are related to hemostasis, clot formation, platelet activation and degranulation, innate immune system, complement activation and leukocyte activation, ECM organization and cell-ECM interaction.

TABLE 2 list of pathways

| Pathway identifier | Pathway name | # Entities found | # Entities total | Entities FDR | # Reactions found | # Reactions total | Reactions ratio |
|---|---|---|---|---|---|---|---|
| R-HSA-168249 | Innate Immune System | 53 | 956 | 0.01810376 | 154 | 615 | 0.071007967 |
| R-HSA-109582 | Hemostasis | 47 | 526 | 0.00000474 | 99 | 310 | 0.035792634 |
| R-HSA-5653656 | Vesicle-mediated transport | 38 | 520 | 0.00195674 | 54 | 138 | 0.015933495 |
| R-HSA-76002 | Platelet activation, signaling and aggregation | 35 | 230 | 7.55E−10 | 43 | 113 | 0.013046992 |
| R-HSA-422475 | Axon guidance | 33 | 549 | 0.04037441 | 56 | 261 | 0.030135088 |
| R-HSA-114608 | Platelet degranulation | 30 | 79 | 5.13E−14 | 6 | 10 | 0.001154601 |
| R-HSA-76005 | Response to elevated platelet cytosolic Ca2+ | 30 | 84 | 5.13E−14 | 6 | 13 | 0.001500981 |
| R-HSA-166658 | Complement cascade | 26 | 195 | 0.00000474 | 45 | 57 | 0.006581226 |
| R-HSA-166663 | Initial triggering of complement | 23 | 177 | 0.0000301 | 15 | 20 | 0.002309202 |
| R-HSA-2029480 | Fcgamma receptor (FCGR) dependent phagocytosis | 22 | 242 | 0.00195674 | 24 | 42 | 0.004849325 |
| R-HSA-1474244 | Extracellular matrix organization | 22 | 272 | 0.0066389 | 120 | 273 | 0.03152061 |
| R-HSA-2029482 | Regulation of actin dynamics for phagocytic cup formation | 21 | 217 | 0.00195674 | 13 | 24 | 0.002771043 |
| R-HSA-173623 | Classical antibody-mediated complement activation | 20 | 163 | 0.000288 | 2 | 2 | 0.000231 |
| R-HSA-166786 | Creation of C4 and C2 activators | 20 | 169 | 0.000449 | 2 | 7 | 0.000808 |
| R-HSA-2173782 | Binding and Uptake of Ligands by Scavenger Receptors | 19 | 195 | 0.00195674 | 9 | 32 | 0.003694723 |
| R-HSA-2029481 | FCGR activation | 18 | 169 | 0.00195674 | 6 | 6 | 0.000693 |
| R-HSA-2029485 | Role of phospholipids in phagocytosis | 17 | 182 | 0.0064822 | 5 | 12 | 0.001385521 |
| R-HSA-983695 | Antigen activates B Cell Receptor (BCR) leading to generation of second messengers | 16 | 168 | 0.00708891 | 7 | 17 | 0.001962822 |
| R-HSA-2168880 | Scavenging of heme from plasma | 16 | 166 | 0.00661425 | 3 | 12 | 0.001385521 |
| R-HSA-2871809 | FCERI mediated Ca+2 mobilization | 15 | 185 | 0.03983869 | 5 | 11 | 0.001270061 |
| R-HSA-5690714 | CD22 mediated BCR regulation | 15 | 138 | 0.00315764 | 3 | 4 | 0.000462 |
| R-HSA-373760 | L1CAM interactions | 13 | 117 | 0.00618833 | 23 | 53 | 0.006119386 |
| R-HSA-977225 | Amyloid fiber formation | 12 | 67 | 0.000626 | 10 | 25 | 0.002886503 |
| R-HSA-140877 | Formation of Fibrin Clot (Clotting Cascade) | 12 | 39 | 0.00000549 | 26 | 53 | 0.006119386 |
| R-HSA-216083 | Integrin cell surface interactions | 12 | 85 | 0.00195674 | 22 | 55 | 0.006350306 |
| R-HSA-437239 | Recycling pathway of L1 | 10 | 47 | 0.000756 | 13 | 14 | 0.001616442 |
| R-HSA-389958 | Cooperation of Prefoldin and TriC/CCT in actin and tubulin folding | 10 | 31 | 0.0000329 | 6 | 6 | 0.000693 |
| R-HSA-390466 | Chaperonin-mediated protein folding | 10 | 52 | 0.00121885 | 8 | 8 | 0.000924 |
| R-HSA-391251 | Protein folding | 10 | 58 | 0.00195674 | 17 | 17 | 0.001962822 |
| R-HSA-389957 | Prefoldin mediated transfer of substrate to CCT/TriC | 9 | 26 | 0.0000595 | 2 | 2 | 0.000231 |
| R-HSA-389960 | Formation of tubulin folding intermediates by CCT/TriC | 9 | 24 | 0.0000338 | 2 | 2 | 0.000231 |
| R-HSA-5674135 | MAP2K and MAPK activation | 8 | 40 | 0.00195674 | 4 | 8 | 0.000924 |
| R-HSA-75153 | Apoptotic execution phase | 8 | 52 | 0.00876007 | 9 | 54 | 0.006234846 |
| R-HSA-432720 | Lysosome Vesicle Biogenesis | 8 | 37 | 0.00195674 | 6 | 8 | 0.000924 |
| R-HSA-190828 | Gap junction trafficking | 8 | 48 | 0.00605815 | 7 | 20 | 0.002309202 |
| R-HSA-157858 | Gap junction trafficking and regulation | 8 | 50 | 0.0072816 | 7 | 24 | 0.002771043 |
| R-HSA-140837 | Intrinsic Pathway of Fibrin Clot Formation | 7 | 22 | 0.00102845 | 11 | 18 | 0.002078282 |

TABLE 2-continued list of pathways

| Pathway identifier | Pathway name | # Entities found | # Entities total | Entities FDR | # Reactions found | # Reactions total | Reactions ratio |
|---|---|---|---|---|---|---|---|
| R-HSA-174824 | Lipoprotein metabolism | 7 | 28 | 0.00195674 | 31 | 42 | 0.004849325 |
| R-HSA-76009 | Platelet Aggregation (Plug Formation) | 7 | 37 | 0.00652542 | 21 | 27 | 0.003117423 |
| R-HSA-140875 | Common Pathway of Fibrin Clot Formation | 7 | 22 | 0.00102845 | 15 | 27 | 0.003117423 |
| R-HSA-445355 | Smooth Muscle Contraction | 7 | 33 | 0.00357064 | 5 | 9 | 0.001039141 |
| R-HSA-390450 | Folding of actin by CCT/TriC | 7 | 9 | 0.00000798 | 2 | 2 | 0.000231 |
| R-HSA-372708 | p130Cas linkage to MAPK signaling for integrins | 6 | 15 | 0.00102845 | 3 | 3 | 0.000346 |
| R-HSA-354194 | GRB2:SOS provides linkage to MAPK signaling for Integrins | 6 | 15 | 0.00102845 | 2 | 2 | 0.000231 |
| R-HSA-354192 | Integrin alphaIIb beta3 signaling | 6 | 27 | 0.00661425 | 20 | 24 | 0.002771043 |
| R-HSA-2129379 | Molecules associated with elastic fibres | 6 | 38 | 0.03069938 | 8 | 10 | 0.001154601 |
| R-HSA-977606 | Regulation of Complement cascade | 6 | 24 | 0.00417026 | 27 | 29 | 0.003348343 |
| R-HSA-3299685 | Detoxification of Reactive Oxygen Species | 6 | 30 | 0.01041516 | 5 | 28 | 0.003232883 |
| R-HSA-390471 | Association of TriC/CCT with target proteins during biosynthesis | 6 | 29 | 0.00876007 | 2 | 2 | 0.000231 |
| R-HSA-174800 | Chylomicron-mediated lipid transport | 5 | 14 | 0.00267305 | 10 | 12 | 0.001385521 |
| R-HSA-3000170 | Syndecan interactions | 5 | 27 | 0.03465572 | 5 | 15 | 0.001731902 |
| R-HSA-211227 | Activation of DNA fragmentation factor | 5 | 13 | 0.00195674 | 4 | 11 | 0.001270061 |
| R-HSA-140342 | Apoptosis induced DNA fragmentation | 5 | 13 | 0.00195674 | 4 | 11 | 0.001270061 |
| R-HSA-196025 | Formation of annular gap junctions | 5 | 11 | 0.00195674 | 2 | 2 | 0.000231 |
| R-HSA-190873 | Gap junction degradation | 5 | 12 | 0.00195674 | 4 | 4 | 0.000462 |
| R-HSA-5099900 | WNT5A-dependent internalization of FZD4 | 4 | 15 | 0.02447424 | 2 | 5 | 0.000577 |
| R-HSA-194223 | HDL-mediated lipid transport | 4 | 16 | 0.03079284 | 21 | 22 | 0.002540122 |
| R-HSA-75205 | Dissolution of Fibrin Clot | 4 | 13 | 0.01608075 | 13 | 19 | 0.002193742 |
| R-HSA-3371568 | Attenuation phase | 4 | 14 | 0.02102031 | 3 | 5 | 0.000577 |
| R-HSA-5625900 | RHO GTPases activate CIT | 4 | 17 | 0.03814228 | 5 | 5 | 0.000577 |
| R-HSA-446353 | Cell-extracellular matrix interactions | 4 | 18 | 0.04206956 | 4 | 10 | 0.001154601 |
| R-HSA-177504 | Retrograde neurotrophin signalling | 4 | 13 | 0.01608075 | 3 | 3 | 0.000346 |
| R-HSA-174577 | Activation of C3 and C5 | 3 | 7 | 0.02447424 | 3 | 3 | 0.000346 |
| R-HSA-168274 | Export of Viral Ribonucleoproteins from Nucleus | 3 | 9 | 0.04206956 | 3 | 5 | 0.000577 |

The invention claimed is:

1. A method for preparing a modified, decellularized blood clot comprising:
   (a) obtaining a blood clot; and
   (b) removing the cells of said blood clot by incubating the blood clot with at least one agent selected from the group consisting of a solubilizing agent, a detergent, a hypertonic solution, a hypotonic solution, and any combination thereof,
thereby obtaining a modified, decellularized blood clot, wherein said decellularized blood clot is characterized by:
   (i) having a porous, fibrin matrix;
   (ii) being insoluble;
   (iii) being a three-dimensional scaffold; and
   (iv) comprising at least one biomolecule, wherein said biomolecule is a plasma-derived biomolecule, an activated platelet-derived biomolecule and/or an activated white blood cell (WBC)-derived biomolecule.

2. The method of claim 1, wherein said blood clot is formed in vivo at a site of bleeding.

3. The method of claim 1, wherein said blood clot is formed ex vivo from a blood sample or a blood product obtained from a donor.

4. The method of claim 3, wherein said blood sample is incubated in the absence of an anti-coagulation agent, or in the presence of at least one anticoagulant prior to clot formation.

5. The method of claim 4, wherein at least one agent capable of reversing the action of the anticoagulant is added to the blood sample after the blood sample is incubated in the presence of the at least one anticoagulant.

6. The method of claim 3, wherein the blood sample is further incubated in the presence of a coagulation activator.

7. The method of claim 1, wherein the method further comprises prior to step (a) a pre-modification step comprising exposing blood or a blood product prior to clotting to one or more pre-modifying agents, wherein said pre-modification step comprises incorporating additional biomolecules or eliminating existing biomolecules, and wherein the pre-modifying agent is selected from a group consisting of a biomolecule, a drug, an antigen, a microbe, and a cell.

8. The method of claim 1, wherein the method further comprises, after step (b), step (c) of processing the modified, decellularized blood clot, thereby obtaining a processed modified, decellularized blood clot, wherein the processing step is selected from the group consisting of dehydration, lyophilization, cryopreservation, partial or complete digestion, purification, fractionation, lysis and any combination thereof.

9. The method of claim 1, wherein the method further comprises, after step (b), step (c) of seeding cells or cell aggregates onto the modified, decellularized blood clot, and optionally step (d) of eliminating the cells or cell aggregates from the modified, decellularized blood clot, thereby changing at least one biological and/or mechanical property of the modified, decellularized blood clot.

10. A method of entrapping at least one biomolecule within an insoluble biocompatible scaffold, said method comprising:
(a) obtaining a blood clot; and
(b) removing the cells of said blood clot by incubating the blood clot with at least one agent selected from the group consisting of a solubilizing agent, a detergent, a hypertonic solution, a hypotonic solution, and any combination thereof, thereby obtaining a modified, decellularized blood clot, wherein said modified, decellularized blood clot is characterized by being insoluble, biocompatible and comprising at least one biomolecule entrapped therein, wherein the at least one biomolecule is a plasma-derived biomolecule, an activated platelet-derived biomolecule and/or an activated white blood cell-derived biomolecule.

* * * * *